United States Patent [19]

Broadhurst et al.

[11] 4,393,221
[45] Jul. 12, 1983

[54] PROCESS TO PRODUCE HEXAHYDRONAPHTHACENE DERIVATIVES

[75] Inventors: Michael J. Broadhurst, Baldock; Cedric H. Hassall, Welwyn; Gareth J. Thomas, Luton, all of England

[73] Assignee: Hoffmann-La Roche Inc., Nutley, N.J.

[21] Appl. No.: 318,172

[22] Filed: Nov. 4, 1981

Related U.S. Application Data

[62] Division of Ser. No. 111,348, Jan. 11, 1980, Pat. No. 4,316,985.

[30] Foreign Application Priority Data

Jan. 16, 1979 [GB] United Kingdom ................. 7901537
Jul. 26, 1979 [GB] United Kingdom ................. 7926151

[51] Int. Cl.$^3$ .................... C07C 50/22; C07D 317/72; C07D 339/06
[52] U.S. Cl. .................................... 549/39; 260/351; 260/351.1; 260/351.5; 549/336; 549/338
[58] Field of Search .................... 549/39, 336, 338; 260/351, 351.1, 351.5

[56] References Cited

U.S. PATENT DOCUMENTS 4,116,981  9/1978  Kende ............................ 260/346.71
4,196,127  4/1980  Johnson et al. ..................... 260/351
4,316,985  2/1982  Broadhurst et al. ................... 549/39

FOREIGN PATENT DOCUMENTS 470334  5/1969  Switzerland ......................... 260/351

OTHER PUBLICATIONS

Lee et al., J. Org. Chem., 41 (3), 1976, pp. 2296-2303.
Farina et al.; Tetrahedron Letters, No. 17, 1972, pp. 1655-1658.
Kende et al.; Tetrahedron Letters, No. 40, 1977, pp. 3537-3540.

Primary Examiner—Joseph Paul Brust
Attorney, Agent, or Firm—Jon S. Saxe; Bernard S. Leon; Frank P. Hoffman

[57] ABSTRACT

There is presented a process for the manufacture of hexahydronaphthacene derivatives of the general formula wherein one of $R^1$ and $R^2$ represents a hydrogen atom and the other represents a hydrogen atom or a hydroxy group or $R^1$ and $R^2$ together represent a protected oxo group, $R^3$ represents a hydrogen atom or a hydroxy or acyloxy group and $R^4$ represents a lower alkyl or esterified carboxy group or a group of the formula $$\begin{array}{c} R^5 \quad R^6 \\ \diagdown \diagup \\ -C-CH_2-X \end{array} \qquad a$$

wherein $R^5$ and $R^6$ together form an oxo group or a protected oxo group and X represents a hydrogen atom or a hydroxy or acyloxy group or $$-(CH_2)_n-OY \qquad b$$

in which n stands for 1 or 2 and Y represents a hydrogen atom or an alkyl or acyl group.

Also presented are certain of the novel derivatives per se and various novel intermediates in the process.

3 Claims, No Drawings

PROCESS TO PRODUCE HEXAHYDRONAPHTHACENE DERIVATIVES

This is a division, of application Ser. No. 111,348 filed Jan. 11, 1980 now U.S. Pat. No. 4,316,985 issued Feb. 23, 1982.

DESCRIPTION OF THE INVENTION

The present invention relates to cyclic compounds. More particularly, the invention is concerned with a process for the manufacture of hexahydronaphthacene derivatives and with certain of said derivatives per se. The invention is also concerned with novel intermediates occurring in said process and with the preparation thereof.

The hexahydronaphthacene derivatives obtained in accordance with the present invention are compounds of the general formula

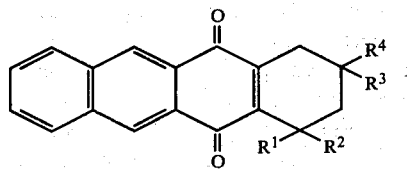

I wherein one of $R^1$ and $R^2$ represents a hydrogen atom and the other represents a hydrogen atom or a hydroxy group or $R^1$ and $R^2$ together represent a protected oxo group, $R^3$ represents a hydrogen atom or a hydroxy or acyloxy group and $R^4$ represents a lower alkyl or esterified carboxy group or a group of the formula

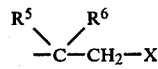

a wherein $R^5$ and $R^6$ together form an oxo group or a protected oxo group and X represents a hydrogen atom or a hydroxy or acyloxy group or or

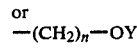

b in which n stands for 1 or 2 and Y represents a hydrogen atom or an alkyl or acyl group.

The term "lower alkyl" means a straight-chain or branched-chain alkyl group which preferably contains from 1 to 6 carbon atoms such as methyl, ethyl, propyl, isopropyl, butyl, tert.butyl, pentyl, hexyl etc.

A protected oxo group in the foregoing formula can be any conventional protected oxo group. Preferably, an oxo group is protected in the form of a ketal or thioketal, especially an alkylene ketal or alkylene thioketal. An esterified carboxy group can be an alkoxycarbonyl group (e.g. methoxycarbonyl, ethoxycarbonyl etc), an aryloxycarbonyl group (e.g. phenoxycarbonyl etc) or an aralkoxycarbonyl group (e.g. benzyloxycarbonyl etc). The methoxycarbonyl group is the preferred alkoxycarbonyl group. The acyl moiety of an acyloxy group can be derived from an alkanecarboxylic acid (e.g. acetic acid, propionic acid etc), an aromatic carboxylic acid (e.g. benzoic acid etc) or an araliphatic carboxylic acid (e.g. phenylacetic acid etc).

According to the present invention, the compounds of formula I hereinbefore are manufactured by either (a) eliminating 2 mols of the carboxylic acid $R^7H$ from a compound of the general formula

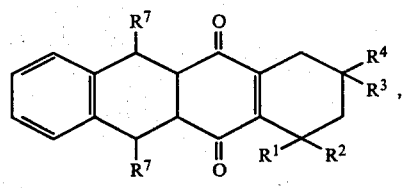

II wherein $R^1$, $R^2$, $R^3$ and $R^4$ have the significance given earlier and $R^7$ represents an acyloxy group, by heating or treatment with a base, or (b) reacting a compound of the general formula

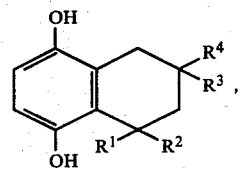

III wherein $R^1$, $R^2$, $R^3$ and $R^4$ have the significance given earlier, with the dialdehyde of the formula

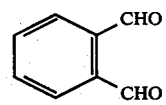

IV in the presence of an aromatic boronic acid.

The heating of a compound of formula II in accordance with embodiment (a) of the foregoing process is preferably carried out in an inert organic solvent. Preferred among the solvents which can be used for this purpose are aromatic hydrocarbons such as benzene, toluene and xylene. The heating is preferably carried out at the reflux temperature of the mixture. If desired, the heating may be carried out under the atmosphere of an inert gas such as nitrogen or argon. In a preferred aspect of this embodiment, a compound of formula II is heated in situ; that is to say, without isolation from the medium in which it is prepared.

The treatment of a compound of formula II with a base, also in accordance with embodiment (a) of the foregoing process, can be carried out using an inorganic base or an organic base. It is preferred to carry out this treatment using an inorganic base, particularly an alkali metal hydroxide such as sodium hydroxide or potassium hydroxide, in a lower alkanol (e.g. methanol or ethanol). This treatment is conveniently carried out at about room temperature.

The reaction of a compound of formula III with the dialdehyde of formula IV, i.e. phthalaldehyde, in accordance with embodiment (b) of the foregoing process, is preferably carried out in an inert organic solvent. The preferred solvents are aromatic hydrocarbons such as benzene, toluene and xylene. Of the aromatic boronic acids which can be used in this reaction benzeneboronic acid is preferred. However, other aromatic boronic acids such as a tolueneboronic acid, xyleneboronic acid, methoxybenzeneboronic acid, nitrobenzeneboronic acid, pyridineboronic acid or the like can also be used. It is convenient to carry out the reaction in the presence of a catalytic amount of a carboxylic acid, preferably a lower alkanecarboxylic acid such as acetic acid, propionic acid etc. The reaction is advantageously carried out at an elevated temperature, suitably at the reflux temperature of the reaction mixture. If desired, the reaction can be carried out under the atmosphere of an inert gas such as nitrogen or argon.

It will be appreciated that certain compounds falling within formula I can be converted into other compounds falling within formula I. These conversions can be carried out in a generally known manner.

In one particular embodiment, a compound of formula I in which one of $R^1$ and $R^2$ represents a hydrogen atom and the other represents a hydroxy group, $R^3$ represents a hydroxy group and $R^4$ represents an acetyl group can be brominated and the bromine atom in the resulting bromoacetyl compound can be displaced by an acyloxy group to give a compound of formula I in which one of $R^1$ and $R^2$ represents a hydrogen atom and the other represents a hydroxy group, $R^3$ represents a hydroxy group and $R^4$ represents a group of formula (a) wherein $R^5$ and $R^6$ together form an oxo group and X represents an acyloxy group.

The bromination can be carried out according to known methods. In a preferred aspect, the bromination is carried out using elemental bromine in a halogenated hydrocarbon solvent (e.g. chloroform) at about room temperature. Other brominating agents which are suitable for the bromination of ketones can also be used (e.g. pyrrolidone trihydrobromide and trimethylphenylammonium tribromide).

The displacement of the bromine atom in the resulting bromoacetyl compound can be carried out in a manner known per se; for example, by reaction with an alkali metal salt (e.g. the sodium or potassium salt) or the silver salt of the acid corresponding to the acyloxy group to be introduced in the presence of the corresponding acid. It is preferred to use the silver salt. Suitable solvents in which this displacement can be carried out include acetonitrile, dimethyl sulphoxide etc. This displacement can be carried out at room temperature or at an elevated temperature depending on the reactants used.

When the aforementioned displacement is carried out to give a compound of formula I in which X represents a perfluoroalkanoyl group (e.g. trifluoroacetyl), this compound can be hydrolysed simply by treatment with water. There is thus obtained a corresponding compound of formula I in which X represents a hydroxy group.

The starting materials of formula II hereinbefore can be prepared, also in accordance with the present invention, by reacting a compound of the general formula

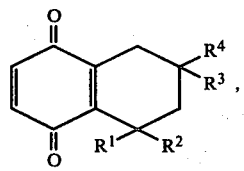

V wherein $R^1$, $R^2$, $R^3$ and $R^4$ have the significance given earlier,
with a trans compound of the general formula

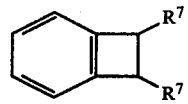

VI wherein $R^7$ has the significance given earlier.

The reaction of a compound of formula V with a trans compound of formula VI to give a compound of formula II is suitably carried out in an inert organic solvent, especially an aromatic hydrocarbon such as benzene, toluene or xylene. It is preferred to carry out this reaction at an elevated temperature, conveniently at the reflux temperature of the reaction mixture. If desired, the reaction can be carried out under the atmosphere of an inert gas such as nitrogen or argon.

The starting materials of formula III hereinbefore can be prepared, also in accordance with the present invention, by catalytically hydrogenating a compound of formula V hereinbefore.

The catalytic hydrogenation of a compound of formula V can be carried out in a manner known per se, conveniently using hydrogen in the presence of a noble metal catalyst such as a palladium or platinum catalyst, preferably a palladium catalyst (e.g. palladium-on-carbon), in an inert organic solvent (e.g. a lower alkanol such as methanol) at room temperature and atmospheric pressure. The mixture obtained after the catalytic hydrogenation can be worked-up in a conventional manner; for example, by filtration, evaporation of the filtrate and, where required, recrystallisation from a suitable solvent.

According to a further embodiment of the present invention, the compounds of formula V hereinbefore can be prepared by treating a compound of the general formula

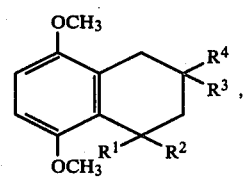

VII wherein $R^1$, $R^2$, $R^3$ and $R^4$ have the significance given earlier,
with ammonium ceric nitrate.

The treatment of a compound of formula VII with ammonium ceric nitrate is conveniently carried out in a mixture of water and a water-miscible inert organic solvent (e.g. acetonitrile or the like). The treatment is advantageously carried out at about room temperature.

The compounds of formula VII hereinbefore can be prepared by a variety of routes.

For example, compounds of formula VII in which $R^1$ and $R^2$ each represent a hydrogen atom can be prepared on the basis of Formula Scheme I hereinafter in which $R^{31}$ represents an acyloxy group, $R^{41}$ represents an esterified carboxy group and $R^{42}$ represents an acyloxyacetyl group.

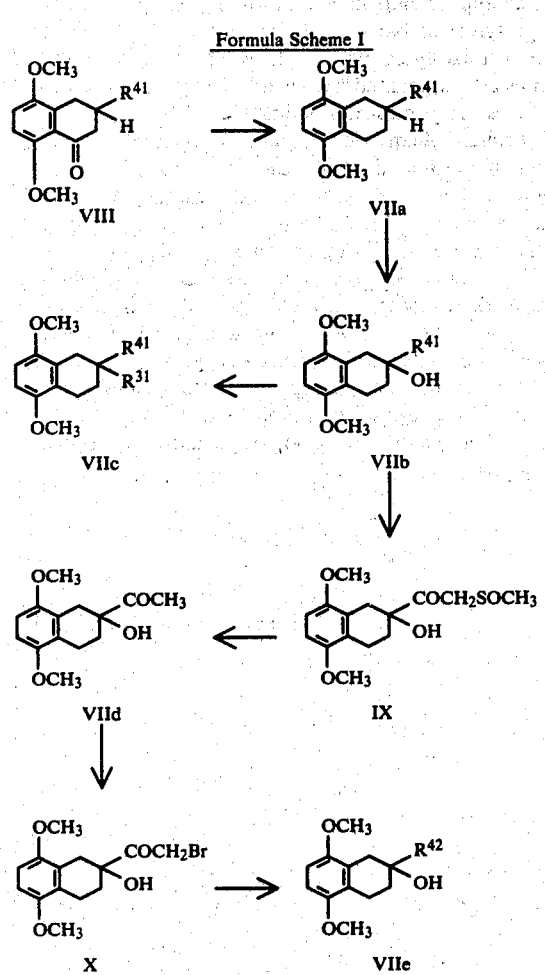

Formula Scheme I

Having regard to Formula Scheme I, a compound of formula VIII, which is a known compound or an analogue of a known compound, is converted into a compound of formula VIIa by catalytic hydrogenation.

The catalytic hydrogenation of a compound of formula VIII can be carried out in a manner known per se; for example, using hydrogen in the presence of a palladium catalyst (e.g. palladium-on-carbon) in a suitable solvent such as ethyl acetate or the like.

A compound of formula VIIa is converted into a compound of formula VIIb by first forming the lithium enolate of a compound of formula VIIa and then treating the enolate either with diperoxo-oxohexamethylphosphoramidomolybdenum (VI) pyridine (MoO$_5$.-py.HMPT) or with oxygen in the presence of a trialkylphosphite.

The conversion of a compound of formula VIIa into a lithium enolate is carried out in a manner known per se; for example, using lithium diisopropylamide in an inert organic solvent such as tetrahydrofuran at a low temperature (e.g. −78° C.).

The lithium enolate is then treated, preferably in situ, either with the diperoxo-oxohexamethylphosphoramidomolybdenum (VI) pyridine, suitable at a temperature between about room temperature and −78° C., or with oxygen in the presence of a trialkylphosphite (e.g. triethylphosphite), suitably by passing oxygen gas through a mixture of the enolate and the trialkylphosphite in an inert organic solvent such as tetrahydrofuran at a low temperature (e.g. −78° C.).

A compound of formula VIIb can be acylated to give a compound of formula VIIc. The acylation of a compound of formula VIIb can be carried out according to known methods; for example, using an appropriate acid or a reactive functional derivative thereof in the presence of an acid-binding agent. Examples of reactive functional derivatives of acids which can be used are acid halides, preferably acid chlorides, acid anhydrides and the like, the preferred reactive functional derivatives being acid anhydrides. Preferred acid-binding agents are tertiary organic bases such as triethylamine, pyridine, 4-dimethylaminopyridine etc. The acylation can be carried out in the presence of an inert organic solvent, but in a preferred embodiment it is carried out using an excess of a tertiary organic base, preferably pyridine, which simultaneously serves both as the acid-binding agent and as the solvent.

A compound of formula VIIb can be converted into a β-ketosulphoxide of formula IX by treatment with an alkali metal salt of dimethyl sulphoxide. This treatment is preferably carried out using the sodium salt of dimethyl sulphoxide and in an inert organic solvent (e.g. tetrahydrofuran) at about 0° C.

A compound of formula IX is then converted into a compound of formula VIId by treatment with aluminium amalgam. This treatment is suitably carried out in the presence of an inert solvent (e.g. aqueous tetrahydrofuran) at a temperature between about 10° C. and 20° C. If desired, this treatment can be carried out under the atmosphere of an inert gas such as nitrogen or argon.

A compound of formula VIId can then be brominated to give a compound of formula X. This bromination can be carried out according to known methods. A preferred brominating agent is pyrrolidone trihydrobromide, although other brominating agents which are suitable for the bromination of ketones (e.g. trimethylphenylammonium tribromide) can also be used.

The bromine atom in a compound of formula X can subsequently be displaced by an acyloxy group to give a compound of formula VIIe. This displacement can be carried out according to known methods, for example, by reaction with the silver salt of the acid corresponding to the acyloxy group to be introduced in the presence of the corresponding acid.

Compounds of formula VII in which R$^1$ and R$^2$ together represent a protected oxo group can be prepared on the basis of Formula Scheme II hereinafter in which R$^{10}$ and R$^{20}$ together represent a protected oxo group, R$^{50}$ and R$^{60}$ together represent a protected oxo group and R$^{31}$ and R$^{41}$ have the significance given earlier.

Formula Scheme II

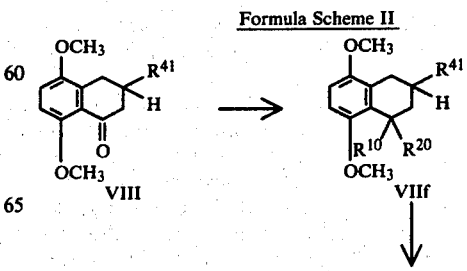

-continued
Formula Scheme II

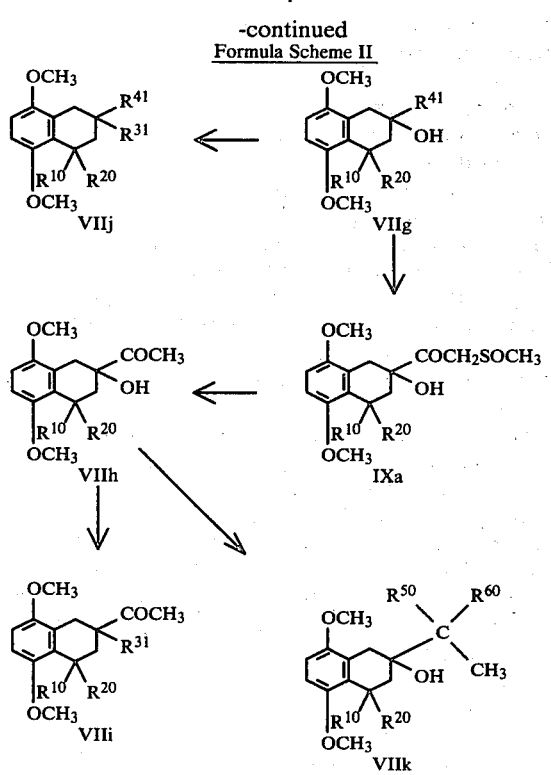

Having regard to Formula Scheme II, a compound of formula VIII is converted into a compound of formula VIIf in a manner known per se for the protection of an oxo group. In a preferred embodiment, this conversion comprises a ketalisation which can be carried out, for example, using an appropriate alcohol or alkylenediol in the presence of toluene-4-sulphonic acid and in the presence of a suitable inert organic solvent such as an aromatic hydrocarbon (e.g. benzene toluene etc) at an elevated temperature (e.g. at the reflux temperature of the reaction mixture). Preferably, a compound of formula VIIf in which $R^{10}$ and $R^{20}$ together represent an alkylenedioxy group, especially the ethylenedioxy group, is prepared.

The subsequent conversion of a compound of formula VIIf into a compound of formula VIIj or into a compound of formula VIIh can be carried out in an analogous manner as described in the respective steps of Formula Scheme I.

A compound of formula VIIh can be acylated to give a compound of formula VIIi. This acylation can be carried out in an analogous manner to that described earlier in connection with the acylation of a compound of formula VIIb to give a compound of formula VIIc.

Alternatively, a compound of formula VIIh can be converted by protection of the oxo group into a compound of formula VIIk. This step can be carried out in an analogous manner to that described earlier in connection with the conversion of a compound of formula VIII into a compound of formula VIIf.

A compound of formula VII depicted in Formula Scheme II in which $R^{10}$ and $R^{20}$ together represent an alkylenedioxy group, especially the ethylenedioxy group, can be converted into a corresponding compound of formula VII in which $R^{10}$ and $R^{20}$ together represent an alkylenedithio group, especially the ethylenedithio group. This conversion can be carried out by treating the alkylenedioxy-substituted compound with an appropriate alkanedithiol (e.g. ethanedithiol) in the presence of boron trifluoride etherate. This treatment is suitably carried out in an inert organic solvent such as a halogenated hydrocarbon (e.g. dichloromethane) at a temperature of about 0° C.

Formula Scheme III hereinafter illustrates the preparation of compounds of formula VII in which one of $R^1$ and $R^2$ represents a hydrogen atom and the other represents a hydroxy group, $R^3$ represents a hydroxy group and $R^4$ represents a group of formula (a) hereinbefore in which $R^5$ and $R^6$ together represent an alkylenedioxy group and X represents a hydrogen atom. In Formula Scheme III, $R^{11}$ and $R^{21}$ represent an alkylenedithio group, especially the ethylenedithio group, one of $R^{12}$ and $R^{22}$ represents a hydrogen atom and the other represents a hydroxy group and $R^{51}$ and $R^{61}$ together represent an alkylenedioxy group, especially the ethylenedioxy group.

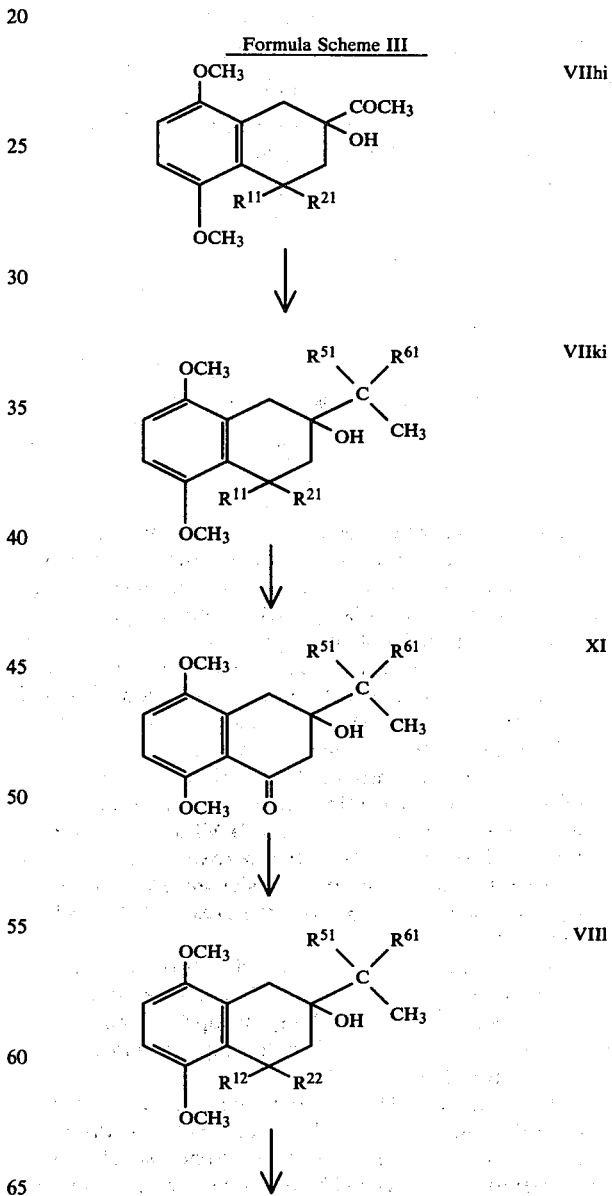

Having regard to Formula Scheme III, a compound of formula VIIhi, prepared, for example, as described in Formula Scheme II, is treated with an alkyleneglycol, preferably ethyleneglycol, in the presence of toluene-4-sulphonic acid to give a compound of formula VIIki. This treatment can be carried out under the same conditions as described earlier in connection with the conversion of a compound of formula VIII into a compound of formula VIIf.

A compound of formula VIIki is then converted into a compound of formula XI by treatment with a mercuric salt, preferably a mixture of mercuric chloride and mercuric oxide. This treatment is suitably carried out in a water-miscible inert organic solvent such as an alkanol (e.g. methanol, ethanol etc), tetrahydrofuran etc or in a mixture of such solvents which may also contain water. The treatment is preferably carried out at room temperature.

A compound of formula XI is subsequently reduced in a manner known per se to give a compound of formula VIII. This reduction is conveniently carried out using an alkali metal borohydride, preferably lithium borohydride, in a customary inert organic solvent such as tetrahydrofuran. Conveniently, this reaction is carried out at room temperature. If desired, the reduction can be carried out under the atmosphere of an inert gas such as nitrogen or argon.

Compounds of formula VII in which $R^4$ represents a group of formula (b) hereinbefore wherein n stands for 1 and Y represents a hydrogen atom can be prepared, for example, by reducing a compound of formula VII in which $R^4$ represents an esterified carboxy group (e.g. a compound of formula VIIg) in a manner known per se. For example, the reduction can be carried out using an alkali metal borohydride such as sodium borohydride in an inert organic solvent such as tetrahydrofuran etc.

A compound of formula VII in which $R^4$ represents a group of formula (b) wherein n stands for 1 and Y represents a hydrogen atom can be appropriately etherified to give a compound of formula VII in which $R^4$ represents a group of formula (b) wherein n stands for 1 and Y represents an alkyl group. The etherification can be carried out in a manner known per se; for example, with an alkyl halide (e.g. methyl iodide) in the presence of a base (e.g. sodium hydride) and in an inert organic solvent such as dioxan, tetrahydrofuran, 1,2-dimethoxyethane etc).

A compound of formula VII in which $R^4$ represents a group of formula (b) wherein n stands for 1 and Y represents a hydrogen atom can be acylated to give a compound of formula VII in which $R^4$ represents a group of formula (b) wherein n stands for 1 and Y represents an acyl group. This acylation can be carried out in the same manner as described earlier in connection with the acylation of a compound of formula VIIb to give a compound of formula VIIc.

Compounds of formula VII in which $R^4$ represents a group of formula (b) hereinbefore wherein n stands for 2 and Y represents a hydrogen atom can be prepared, for example, by first converting a compound of formula VII in which n stands for 1 and Y represents a hydrogen atom into a compound of the general formula

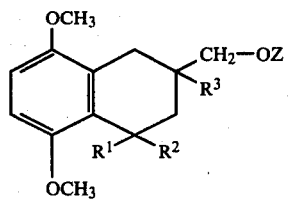

wherein $R^1$, $R^2$ and $R^3$ have the significance given earlier and Z represents a lower alkylsulphonyl or arylsulphonyl group.

This conversion can be carried out in a manner known per se; for example, by reaction with a lower alkylsulphonyl chloride (e.g. methanesulphonyl chloride) or, preferably, with an arylsulphonyl chloride (e.g. toluene-4-sulphonyl chloride) in the presence of an appropriate base (e.g. a tertiary amine such as pyridine, 4-dimethylaminopyridine etc) and at a low temperature (e.g. 0°–5° C.

In the next step, a compound of formula XII is treated with an alkali metal cyanide to give a compound of the general formula

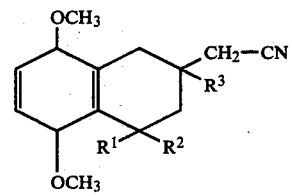

wherein $R^1$, $R^2$ and $R^3$ have the significance given earlier.

This treatment is carried out in a known manner; for example, using potassium cyanide in aqueous dimethyl sulphoxide or dimethylformamide.

A compound of formula XIII is then hydrolysed to give a compound of the general formula

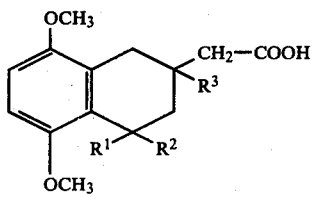

wherein $R^1$, $R^2$ and $R^3$ have the significance given earlier.

This hydrolysis is carried out in a manner known per se for the hydrolysis of nitriles to the corresponding acids; for example, using an alkali metal hydroxide such as potassium hydroxide in an aqueous lower alkanol such as aqueous ethanol.

Finally, a compound of formula XIV is converted by reduction into a desired compound of formula VII in which $R^4$ represents a group of formula (b) wherein n stands for 2 and Y represents a hydrogen atom. This reduction can be carried out in a manner known per se for the reduction of carboxylic acids to corresponding alcohols. Thus, for example, the reduction can be carried out using an alkali metal aluminium hydride (e.g. lithium aluminium hydride) in an inert organic solvent (e.g. tetrahydrofuran, dioxan etc). Again, for example, the reduction can be carried out using diborane. In certain circumstances if can be advantageous to convert a compound of formula XIV into an ester (e.g. the methyl ester) prior to the reduction.

A compound of formula VII in which R⁴ represents a group of formula (b) wherein n stands for 2 and Y represents a hydrogen atom can be appropriately etherified or acylated to give a compound of formula VII in which R⁴ represents a group of formula (b) wherein n stands for 2 and Y represents an alkyl or acyl group. The etherification and the acylation can be carried out in the same manner as indicated earlier in connection with the etherification and esterification of a compound of formula VII in which R⁴ represents a group of formula (b) wherein n stands for 1 and Y represents a hydrogen atom.

Compounds of formula VII in which R⁴ represents a methyl group can be prepared, for example, by reducing a compound of formula XII with an alkali metal aluminium hydride such as lithium aluminium hydride in a known manner. Compounds of formula VII in which R⁴ represents a different lower alkyl group can be prepared similarly from corresponding ω-(lower alkylsulphonyloxy or arylsulphonyloxy)-(lower alkyl) compounds. For example, a lower alkylsulphonate or arylsulphonate derived from an aforementioned compound of formula II in which R⁴ represents a group of formula (b) wherein n stands for 2 and Y represents a hydroxy group can be reduced to give a compound of formula VII in which R⁴ represents an ethyl group. Alternatively, this lower alkylsulphonate or arylsulphonate can be chain-lengthened according to the procedure described earlier (i.e. via a nitrile, acid and alcohol) and then reduced. This chain-lengthening can, of course, be repeated as required.

The novel cyclic compounds of formula

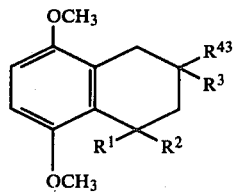

VII' wherein one of R¹ and R² represents a hydrogen atom and the other represents a hydrogen atom or a hydroxy group or R¹ and R² together represent a protected oxo group, R³ represents a hydrogen atom or a hydroxy or acyloxy group and R⁴³ represents a lower alkyl, carboxy or esterified carboxy group or a group of the formula

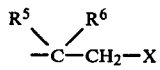
a in which R⁵ and R⁶ together form an oxo group or a protected oxo group and X represents a hydrogen atom or a hydroxy or acyloxy group, or

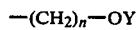
b in which n stands for 1 or 2 and Y represents a hydrogen atom or an alkyl or acyl group, with the provisos (i) that R¹ and R² do not both represent a hydrogen atom or an ethylenedithio group when R³ represents a hydrogen atom and R⁴ represents a carboxy or acetyl group, (ii) that R¹ and R² do not both represent a hydrogen atom when R³ represents a hydroxy group and R⁴ represents a carboxy, methoxycarbonyl or acetyl group, and (iii) that R¹ and R² do not both represent a hydrogen atom when R³ represents an acetoxy group and R⁴ represents an acetyl group,
are a further embodiment of the present invention.

Compounds of formulae I, II, III, V and VII hereinbefore can exist not only in racemic but also in optically active form. It will be appreciated that the invention includes not only the racemates but also the optical isomers. A racemate can be split up into its optical isomers in accordance with methods known per se. For example, a compound in which R⁴ represents an esterified carboxy group can be saponified to the corresponding carboxylic acid (e.g. by treatment with an alkali metal hydroxide such as sodium hydroxide) and the acid can be resolved by salt formation with an appropriate base such as brucine. An optically active acid thus obtained can subsequently be esterified to give a corresponding optically active ester.

Depending on the nature of the substituents present, compounds of formulae, I, II, III, V and VII can exhibit cis/trans isomerism. It will be appreciated that this invention includes the cis and trans isomers as well as mixtures thereof.

In a particular embodiment of the present invention, a cis/trans compound in which one of R¹ and R² represents a hydrogen atom and the other represents a hydroxy group and R³ represents a hydroxy group can be treated with an aromatic boronic acid to give a mixture the cis boronic acid ester and unchanged trans diol. This mixture can be separated and the cis boronic acid ester can be converted into the cis diol. The treatment with an aromatic boronic acid such as one of those mentioned hereinbefore, preferably benzeneboronic acid, is expediently carried out in an inert organic solvent such as ethyl acetate at an elevated temperature, suitably at the reflux temperature of the mixture, and, if desired, under the atmosphere of an inert gas such as nitrogen or argon. The separation of the cis boronic acid ester and trans diol can be carried out by chromatography, suitably on silica gel. The cis boronic acid ester is conveniently converted into the cis diol by treatment with an acid, preferably an organic carboxylic acid such as acetic acid, in the presence of an excess of a 1,3-diol such as 2-methyl-2,4-pentanediol. The treatment is conveniently carried out in an inert organic solvent, preferably a halogenated hydrocarbon such as dichloromethane, and at room temperature.

According to another embodiment of this invention, a trans diol can be converted into a corresponding cis boronic acid ester which, in turn, can be converted into the cis diol. The conversion of the trans diol into the cis boronic acid ester can be carried out by treatment with an aromatic boronic acid such as one of those mentioned earlier, preferably benzeneboronic acid, in the presence of an organic sulphonic acid, preferably an aromatic sulphonic acid such as toluene-4-sulphonic acid. This treatment is advantageously carried out in an inert organic solvent, preferably an aromatic hydrocarbon such as benzene, at about room temperature. This cis boronic acid ester obtained can then be converted into the cis diol in the manner described earlier.

The foregoing separation of a cis/trans mixture into the cis and trans isomers is advantageously carried out on a bicyclic compound, especially a bicyclic compound of formula VII. The individual isomers can be carried through the entire process without change in configuration occurring.

It will be appreciated that when an optically active starting material is used in the process of this invention, the optical configuration is retained during the entire reaction sequence, thus enabling the preparation of isomers with specific chirality at the chiral centre(s) present.

The compounds of formula I hereinbefore are useful as chemical intermediates; for example, in the manufacture of other tetracyclic compounds having antibiotic activity or antitumour activity.

Specific useful compounds for which the present compounds may be utilized as intermediates are 4-demethoxyduanorubicin and 4-demethoxyadriamycin which are disclosed in Belgian Pat. Nos. 830,090 and 842,930 and Chemical Abstracts 87, 8501(1977) and in Cancer Treatment Reports 60, 829(1976).

Certain of the compounds of formula I may also be converted into aglycones of compounds known antineoplastic activity as described by Kende et al., Tetrahedron Letters, No. 30, 3537–3540, 1977 and by Wiseman et al., Tetrahedron Letters, No. 40, 3765–3768, 1977. The aglycones may thereafter be coupled with various sugars following methods set forth by Action et al., J. Med. Chem., 17, 659 (1974) and Arcamone et al., J. Med. Chem. 18, 703 (1975). Further teachings may be found in British Pat. Nos. 1,500,421 and 1,457,559.

The following Examples illustrate the present invention:

EXAMPLE 1

(A) A solution of 4.90 g (0.009 mol) of ammonium ceric nitrate in 20 ml of water was added to a stirred solution of 1.20 g (0.0035 mol) of methyl rac-1',2',3',4'-tetrahydro-5',8'-dimethoxyspiro[1,3-dithiolane-2,4'-naphthalene]-2'-carboxylate in 100 ml of acetonitrile. The mixture was stirred at room temperature for 5 minutes, then diluted with 100 ml of water and extracted with three 200 ml portions of diethyl ether. The combined diethyl ether extracts were washed with water, dried and evaporated to yield 1.23 g of crude product in the form of an orange gum. This was taken up in diethyl ether and crystallised to yield 0.90 g (82%) of methyl rac-1',2',3',4',5',8'-hexahydro-5',8'-dioxospiro[1,3-dithiolane-2,4'-naphthalene]-2'-carboxylate in the form of a bright orange solid of melting point 140°–141° C.

(B) 1.86 g (0.006 mol) of methyl rac-1',2',3',4',5',8'-hexahydro-5',8'-dioxospiro[1,3-dithiolane-2,4'-naphthalene]-2'-carboxylate were warmed in 200 ml of methanol to bring about complete solution. After cooling, 0.40 g of 10% palladium-on-carbon catalyst was added and the mixture was shaken under one atmosphere of hydrogen until hydrogen uptake ceased. The mixture was filtered and the filtrate was evaporated to give 1.83 g of a pale yellow gum. This was taken up in dichloromethane and crystallised to yield 1.10 g (59%) of methyl rac-1',2',3',4'-tetrahydro-5',8'-dihydroxyspiro[1,3-dithiolane-2,4'-naphthalene]-2'-carboxylate in the form of a white crystalline solid of melting point 180°–182° C.

(C) A mixture of 624 mg (2.0 mmol) of methyl rac-1',2',3',4'-tetrahydro-5',8'-dihydroxyspiro[1,3-dithiolane-2,4'-naphthalene]-2'-carboxylate, 268 mg (2.0 mmol) of phthalaldehyde, 488 mg (4.0 mmol) of benzeneboronic acid and 0.3 ml of propionic acid in 25 ml of benzene was stirred and heated under reflux under an atmosphere of nitrogen for 23 hours. The resulting dark red solution was evaporated to give 1.26 g of a dark red solid. This was suspended in 50 ml of dichloromethane and the suspension was filtered. 1 ml of 2-methylpentane-2,4-diol and 0.1 ml of glacial acetic acid were added to the filtrate and the mixture was stirred at room temperature for 2 hours. The solution was then washed with six 25 ml portions of water, two 50 ml portions of 10% sodium metabisulphite solution, two 50 ml portions of a 1:1 mixture of 10% sodium metabisulphite solution and 2-M sodium hydroxide, and finally with two 50 ml portions of water, dried and evaporated to yield 700 mg of crude product in the form of a dark orange gum. This was chromatographed on a column of 27.5 g of Kieselgel 60 using a 1:2 (vol/vol) mixture of diethyl ether and petroleum ether (40°–60° C.) for the elution. There were obtained 263 mg (32%) of methyl rac-1',2',3',4',5',12'-hexahydro-5',12'-dioxospiro[1,3-dithiolane-2,4'-naphthacene]-2'-carboxylate in the form of a bright orange crystalline solid of melting point 216° C.

The methyl rac-1',2',3',4'-tetrahydro-5',8'-dimethoxyspiro[1,3-dithiolane-2,4'-naphthalene]-2'-carboxylate used as the starting material in part (A) of this Example can be prepared by reacting methyl rac-4,4-ethylenedioxy-1,2,3,4-tetrahydro-5,8-dimethoxynaphthalene-2-carboxylate [prepared as described in Example 4(i) hereinafter] with ethanedithiol in a manner analogous to that described in Example 4(iii) hereinafter.

EXAMPLE 2

(A) A solution of 19.74 g (0.036 mol) of ammonium ceric nitrate in 120 ml of water was added to a stirred solution of 3.00 g (0.012 mol) of methyl rac-1,2,3,4-tetrahydro-5,8-dimethoxynaphthalene-2-carboxylate in 54 ml of acetonitrile. The mixture was stirred at room temperature for 25 minutes and then diluted with 150 ml of water. The solution was extracted with three 150 ml portions of diethyl ether and the combined diethyl ether extracts were washed with 150 ml of water, dried and evaporated to yield 2.60 g (98.5%) of methyl rac-1,2,3,4,5,8-hexahydro-5,8-dioxonaphthalene-2-carboxylate in the form of a bright yellow solid of melting point 41°–42° C.

(B) 0.30 g of 10% palladium-on-carbon catalyst was added to a solution of 4.0 g (0.018 mol) of methyl rac-1,2,3,4,5,8-hexahydro-5,8-dioxonaphthalene-2-carboxylate in 180 ml of methanol and the mixture was shaken under one atmosphere of hydrogen until hydrogen uptake ceased (429 ml, 18 minutes). The mixture was filtered and the filtrate was evaporated to yield 4.1 g (100%) of methyl rac-5,8-dihydroxy-1,2,3,4-tetrahydronaphthalene-2-carboxylate in the form of a white crystalline solid of melting point 135°–136° C.

(C) A solution of 4.04 g (0.018 mol) of methyl rac-5,8-dihydroxy-1,2,3,4-tetrahydronaphthalene-2-carboxylate, 2.436 g (0.018 mol) of phthalaldehyde, 4.44 g (0.036 mol) of benzeneboronic acid and 3 ml of propionic acid in 180 ml of benzene was stirred and heated under reflux under an atmosphere of nitrogen for 8.5 hours. The solution was evaporated to give 11.92 g of a red sticky solid. This was triturated with 40 ml of diethyl ether and the resulting red solid was collected to give 2.80 g of product of melting point 158°–167° C. The mother liquor was concentrated to 15 ml and cooled to 0° C. to give a second crop of product weighing 0.80 g. The total yield of methyl rac-1,2,3,4,5,12-hexahydro-5,12- dioxonaphthacene-2-carboxylate was 3.60 g (62%). This was recrystallised from chloroform/petroleum ether (60°–80° C.) to give the pure quinone in the form of a bright yellow solid of melting point 173°–174° C.

EXAMPLE 3

(A) In a manner analogous to that described in Example 1(A), from methyl rac-2-acetoxy-1,2,3,4-tetrahydro-5,8-dimethoxynaphthalene-2-carboxylate there was obtained in 90% yield methyl rac-2-acetoxy-1,2,3,4,5,8-hexahydro-5,8-dioxonaphthalene-2-carboxylate in the form of an orange gum which was used directly in the next step.

(B) In a manner analogous to that described in Example 1(B), from methyl rac-2-acetoxy-1,2,3,4,5,8-hexahydro-5,8-dioxonaphthalene-2-carboxylate there was obtained in 95% yield methyl rac-2-acetoxy-1,2,3,4-tetrahydro-5,8-dihydroxynaphthalene-2-carboxylate.

(C) A mixture of 140 mg (0.5 mmol) of methyl rac-2-acetoxy-1,2,3,4-tetrahydro-5,8-dihydroxynaphthalene-2-carboxylate, 67 mg (0.5 mmol) of phthaladehyde, 122 mg (1.0 mmol) of benzeneboronic acid and 0.1 ml of propionic acid in 12.5 ml of benzene was stirred and heated under reflux for 17 hours under an atmosphere of nitrogen. The solution was then evaporated to yield 337 mg of a dark red sticky solid. This was taken up in 25 ml of dichloromethane and the solution was filtered. 0.5 ml of 2-methylpentane-2,4-diol and 0.1 ml of glacial acetic acid were added to the filtrate and the mixture was stirred at room temperature for 2 hours. The bright orange solution was washed with four 30 ml portions of water, dried and evaporated to yield 244 mg of crude product in the form of a bright yellow solid. This was chromatographed on a column of 10 g of Kieselgel 60 using a 1:2 (vol/vol) mixture of diethyl ether and petroleum ether (40°–60° C.) for the elution. There were obtained 156 mg (82.5%) of methyl rac-2-acetoxy-1,2,3,4,5,12-hexahydro-5,12-dioxonaphthacene-2-carboxylate in the form of a bright yellow solid of melting point 205°–206° C.

The methyl rac-2-acetoxy-1,2,3,4-tetrahydro-5,8-dimethoxynaphthalene-2-carboxylate used as the starting material in part (A) of this Example can be prepared as follows:

(i) According to the procedure described in Example 4(ii)(a) or (b) hereinafter, from methyl rac-1,2,3,4-tetrahydro-5,8-dimethoxynaphthalene-2-carboxylate there was obtained in 67% yield methyl rac-1,2,3,4-tetrahydro-2-hydroxy-5,8-dimethoxynaphthalene-2-carboxylate in the form of colourless crystals of melting point 76.5°–77° C. (from diethyl ether/hexane).

(ii) 5.0 g of methyl rac-1,2,3,4-tetrahydro-2-hydroxy-5,8-dimethoxynaphthalene-2-carboxylate were dissolved in 50 ml of pyridine. The solution was cooled to 0° C. and 10 ml of acetic anhydride and 150 mg of 4-dimethylaminopyridine were added. After standing at 0° C. for 24 hours, the mixture was poured into 250 ml of water. The mixture obtained was extracted with three 100 ml portions of ethyl acetate and the combined ethyl acetate extracts were washed with 2-N hydrochloric acid until the washings were acidic, then with 200 ml of water, 200 ml of dilute aqueous potassium hydrogen carbonate and 200 ml of brine. After drying, the solvent was evaporated to give a white crystalline residue. Recrystallisation from diethyl ether gave 5.6 g (96.5%) of methyl rac-2-acetoxy-1,2,3,4-tetrahydro-5,8-dimethoxynaphthalene-2-carboxylate in the form of colourless crystals of melting point 155.5°–156° C.

EXAMPLE 4

(A) In a manner analogous to that described in Example 1(A), from methyl rac-2'-acetoxy-1',2',3',4'-tetrahydro-5',8'-dimethoxyspiro[1,3-dithiolane-2,4'-naphthalene]-2'-carboxylate there was obtained in 81.5% yield methyl rac-2'-acetoxy-1',2',3',4',5',8'-hexahydro-5',8'-dioxospiro[1,3-dithiolane-2,4'-naphthalene]-2'-carboxylate in the form of an orange solid of melting point 185°–186° C.

(B) In a manner analogous to that described in Example 1(B), from methyl rac-2'-acetoxy-1',2',3',4',5',8'-hexahydro-5',8'-dioxospiro[1,3-dithiolane-2,4'-naphthalene]-2'-carboxylate there was obtained in 85% yield methyl rac-2'-acetoxy-1',2',3',4'-tetrahydro-5',8'-dihydroxyspiro[1,3-dithiolane-2,4'-naphthalene]-2'-carboxylate in the form of an off-white solid of melting point 208°–210° C.

(C) A mixture of 185 mg (0.5 mmol) of methyl rac-2'-acetoxy-1',2',3',4'-tetrahydro-5',8'-dihydroxyspiro[1,3-dithiolane-2,4'-naphthalene]-2'-carboxylate, 122 mg (1.0 mmol) of benzeneboronic acid and 0.1 ml of propionic acid in 7.5 ml of benzene was stirred and heated under reflux under an atmosphere of nitrogen. A solution of 67 mg (0.5 mmol) of phthalaldehyde in 5 ml of benzene was added portionwise over a period of 24 hours. The mixture was stirred and heated under reflux for a further 20 hours and was then evaporated. The dark red residue was taken up in 25 ml of dichloromethane and the solution was filtered. 0.5 ml of 2-methylpentane-2,4-diol and 0.1 ml of glacial acetic acid were added to the filtrate and the mixture was stirred at room temperature for 2 hours. The resulting dark orange solution was washed with four 30 ml portions of water, dried and evaporated to yield 210 mg of an orange gum. This was chromatographed on a column of 10 g of Kieselgel 60 using a 1:2 (vol/vol) mixture of diethyl ether and petroleum ether (40°–60° C.) for the elution. There were obtained 91 mg (39%) of methyl rac-2'-acetoxy-1',2',3',4',5',12'-hexahydro-5',12'-dioxospiro[1,3-dithiolane-2,4'-naphthacene]-2'-carboxylate in the form of a bright yellow solid of melting point 234°–235° C.

The methyl rac-2'-acetoxy-1',2',3',4'-tetrahydro-5',8'-dimethoxyspiro[1,3-dithiolane-2,4'-naphthalene]-2'-carboxylate used as the starting material in part (A) of this Example can be prepared as follows:

(i) 40 g of methyl rac-1,2,3,4-tetrahydro-5,8-dimethoxy-4-oxonaphthalene-2-carboxylate were added to a mixture of 800 ml of toluene, 800 ml of hexane, 30 ml of ethyleneglycol and 0.65 g of toluene-4-sulphonic acid. The mixture was heated under reflux for 24 hours using a Dean-Stark trap. The solution was cooled in an ice-bath and washed with three 124 ml portions of 10% potassium hydrogen carbonate solution and 200 ml of brine, dried and the solvent was evaporated. The residue was taken up in 200 ml of methanol at 70° C. and 0.5 g of a 50% dispersion of sodium hydride in mineral oil was added. The solution obtained was left to cool to room temperature and then cooled further in an ice-bath for 2 hours. The crystalline product was filtered off, washed with cold methanol and dried in vacuo. There were obtained 28.5 g (61%) of methyl rac-4,4-ethylenedioxy-1,2,3,4-tetrahydro-5,8-dimethoxynaphthalene-2-carboxylate in the form of colourless crystals of melting point 133°–134° C.

(ii)(a) To a solution of 84 ml of diisopropylamine in 250 ml of dry tetrahydrofuran at −78° C. under argon was added a solution of n-butyl lithium (39 ml, 1.6 mol)

in hexane. The mixture was stirred for 10 minutes and then a solution of 12.32 g of methyl 4,4-ethylenedioxy-1,2,3,4-tetrahydro-5,8-dimethoxynaphthalene-2-carboxylate in 75 ml of dry tetrahydrofuran was added rapidly. The mixture was held at −78° C. while stirring for 50 minutes and then 27.8 g of finely ground diperoxo-oxohexamethylphosphoramidomolybdenum (VI) pyridine were added. After a further 80 minutes, the mixture was warmed to 0° C. and stirred for 20 minutes before the addition of 400 ml of water. After 10 minutes, most of the tetrahydrofuran was evaporated in vacuo and the aqueous residue was extracted with five 200 ml portions of ethyl acetate. The combined ethyl acetate extracts were dried over magnesium sulphate, filtered and evaporated to give an oil which was purified by chromatography on silica gel using ethyl acetate/hexane (1:1, vol/vol) for the elution. After the elution of 1.57 g of starting material, there were obtained 7.51 g (58%) of methyl rac-4,4-ethylenedioxy-1,2,3,4-tetrahydro-2-hydroxy-5,8-dimethoxynaphthalene-2-carboxylate in the form of colourless crystals of melting point 74°–75° C.

(ii)(b) A solution of the lithium enolate of methyl rac-4,4-ethylenedioxy-1,2,3,4-tetrahydro-5,8-dimethoxynaphthalene-2-carboxylate was prepared in tetrahydrofuran as described in part (ii)(a) of this Example from 9.84 g of methyl rac-4,4-ethylenedioxy-1,2,3,4-tetrahydro-5,8-dimethoxynaphthalene-2-carboxylate. The enolate was added over a period of 5 minutes at −78° C. to a stirred solution of 11.2 ml of dry triethylphosphite in 60 ml of tetrahydrofuran through which a rapid stream of oxygen was passing. The passage of oxygen was maintained for 50 minutes and the temperature was held at −78° C. The reaction was then quenched by the addition of 8.8 ml of acetic acid. The cooling bath was removed and, after 5 minutes, 200 ml of water were added. After a further 20 minutes, most of the tetrahydrofuran was evaporated and the product was extracted into four 100 ml portions of ethyl acetate. The combined ethyl acetate extracts were washed with 200 ml of 10% aqueous potassium hydrogen carbonate, dried over magnesium sulphate, filtered and evaporated to give a yellow oil which was dissolved in 130 ml of ether and left to crystallise. There were obtained 6.86 g (66%) of methyl rac-4,4-ethylenedioxy-1,2,3,4-tetrahydro-2-hydroxy-5,8-dimethoxynaphthalene-2-carboxylate in the form of colourless crystals of melting point 74°–75° C.

(iii) 10 g of methyl rac-4,4-ethylenedioxy-1,2,3,4-tetrahydro-2-hydroxy-5,8-dimethoxynaphthalene-2-carboxylate were dissolved in 30 ml of dichloromethane and the solution was cooled to 0° C. To the solution were added 4 ml of ethanedithiol followed by 4 ml of boron trifluoride etherate. The mixture was stirred at 0° C. for 15 minutes and then poured into 200 ml of diethyl ether. The organic layer was washed with three 50 ml portions of 5% sodium hydroxide solution and evaporated to give a yellow oil which was taken up in 200 ml of methanol. 100 ml of 5% sodium hydroxide solution were added and the resulting solution was stirred at room temperature for 1.5 hours. Most of the methanol was then evaporated, the residue was diluted with 250 ml of water and washed with three 100 ml portions of ether. The aqueous layer was acidified with hydrochloric acid and the precipitated oil was left to solidify. The product was collected by filtration, washed free from acid using water and dried. The crude acid was purified by suspension in 150 ml of ethyl acetate and heating under reflux for 30 minutes. The mixture was cooled and the product was collected by filtration after 24 hours. There were obtained 7.0 g (66.5%) of 1′,2′,3′,4′-tetrahydro-2′-hydroxy-5′,8′-dimethoxyspiro[1,3-dithiolane-2,4′-naphthalene]-2′-carboxylic acid in the form of colourless crystals of melting point 189°–189.5° C.

(iv) 20 g of rac-1′,2′,3′,4′-tetrahydro-2′-hydroxy-5′,8′-dimethoxyspiro[1,3-dithiolane-2,4′-naphthalene]-2′-carboxylic acid were suspended in 200 ml of methanol and 40 ml of boron trifluoride/methanol were added. The mixture was stirred at room temperature for 3.5 hours to give a clear solution. Approximately 80 ml of methanol were removed by evaporation and the remaining solution was poured into 400 ml of dichloromethane. The organic solution was washed with 500 ml of water, 200 ml of 10% potassium hydrogen carbonate solution and 200 ml of brine. After drying over magnesium sulphate, the solvent was removed to give 24 g of a yellow gum. Crystallisation of this gum from diethyl ether/hexane gave 19.5 g (95.5%) of methyl rac-1′,2′,3′,4′-tetrahydro-2′-hydroxy-5′,8′-dimethoxyspiro[1,3-dithiolane-2,4′-naphthalene]-2′-carboxylate of melting point 103.5°–104° C.

(v) In a manner analogous to that described in Example 3(ii), from methyl rac-1′,2′,3′,4′-tetrahydro-2′-hydroxy-5′,8′-dimethoxyspiro[1,3-dithiolane-2,4′-naphthalene]-2′-carboxylate there was obtained in 89% yield methyl rac-2′-acetoxy-1′,2′,3′,4′-tetrahydro-5′,8′-dimethoxyspiro[1,3-dithiolane-2,4′-naphthalene]-2′-carboxylate in the form of colourless crystals of melting point 151°–152° C.

EXAMPLE 5

(A) In a manner analogous to that described in Example 1(A), from rac-3′-acetoxy-3′-acetyl-1,2,3,4-tetrahydro-5′,8′-dimethoxyspiro[1,3-dithiolane-2,1′-naphthalene] there was obtained in 95% yield rac-3′-acetoxy-3′-acetyl-1′,2′,3′,4′,5′,8′-hexahydro-5′,8′-dioxospiro[1,3-dithiolane-2,1′-naphthalene] in the form of orange crystals of melting point 214°–215° C.

(B) In a manner analogous to that described in Example 1(B), from rac-3′-acetoxy-3′-acetyl-1′,2′,3′,4′,5′,8′-hexahydro-5′,8′-dioxospiro[1,3-dithiolane-2,1′-naphthalene] there was obtained in 88% yield rac-3′-acetoxy-3′-acetyl-1′,2′,3′,4′-tetrahydro-5′,8′-dihydroxyspiro[1,3-dithiolane-2,1′-naphthalene] in the form of an off-white solid of melting point 239°–240° C.

(C) A suspension of 177 mg (0.5 mmol) of 3′-acetoxy-3′-acetyl-1′,2′,3′,4′-tetrahydro-5′,8′-dihydroxyspiro[1,3-dithiolane-2,1′-naphthalene], 67 mg (0.5 mmol) of phthalaldehyde and 122 mg (1.0 mmol) of benzeneboronic acid in a mixture of 0.1 ml of propionic acid and 12.5 ml of benzene was stirred and heated under reflux under an atmosphere of nitrogen for 20 hours. The solution was evaporated, the dark red residue was taken up in 35 ml of dichloromethane and the solution was filtered. To the filtrate were added 0.5 ml of 2-methylpentane-2,4-diol and 0.1 ml of glacial acetic acid and the mixture was stirred at room temperature for 2 hours. The solution was washed with four 30 ml portions of water, dried and evaporated to yield 272 mg of a brown gum. This gum was chromatographed on a column of 25 g of Kieselgel 60 using a 1:2 (vol/vol) mixture of diethyl ether and petroleum ether (40°–60° C.) for the elution. There were obtained 54 mg (24%) of rac-3′-acetoxy-3′-acetyl-1′,2′,3′,4′,5′,12′-hexahydro-5′,12′-dioxospiro[1,3-dithiolane-2,1′-naphthacene] in the form of a bright yellow crystalline solid of melting point 239°–241° C.

The rac-3'-acetoxy-3'-acetyl-1',2',3',4'-tetrahydro-5',8'-dimethoxyspiro[1,3-dithiolane-2,1'-naphthalene] used as the starting material in part (A) of this Example can be prepared as follows:

(i) 2.55 g of a 50% dispersion of sodium hydride in mineral oil were added to 30 ml of dry dimethyl sulphoxide stirred under nitrogen. The mixture was stirred at 70° C. until the evolution of hydrogen ceases. After cooling to 0° C., 30 ml of dry tetrahydrofuran were added. 4.0 g of methyl rac-1',2',3',4'-tetrahydro-2'-hydroxy-5',8'-dimethoxyspiro[1,3-dithiolane-2,4'-naphthalene]-2'-carboxylate [prepared as described in Example 4 (iv)] in 30 ml of dry tetrahydrofuran were added dropwise over a period of 10 minutes. After stirring at 0° C. for 15 minutes, the mixture was poured into 200 ml of water and acidified to pH 3 with hydrochloric acid. The solution was extracted with five 100 ml portions of dichloromethane. The combined dichloromethane extracts were washed with 200 ml of water, dried over magnesium sulphate and evaporated to give an orange solid. Trituration of this solid with a mixture of ethyl acetate and diethyl ether gave 3.5 g of crude β-ketosulphoxide in the form of a buff solid which was used without further purification.

3.5 g of the crude β-ketosulphoxide obtained as described in the preceding paragraph were dissolved in 150 ml of tetrahydrofuran containing 15 ml of water. The solution was stirred under nitrogen and cooled to 12° C. Aluminium amalgam (prepared from 3.5 g of aluminium foil) was added and the mixture was stirred for 2 hours while holding the temperature at 12°–15° C. The mixture was then filtered and the tetrahydrofuran was evaporated. The residue was dissolved in ethyl acetate, washed with water, dried and evaporated to give a cream coloured solid. Recrystallisation from dichloromethane/diethyl ether gave 2.5 g (66%) of rac-3'-acetyl-1',2',3',4'-tetrahydro-3'-hydroxy-5',8'-dimethoxyspiro[1,3-dithiolane-2,1'-naphthalene] in the form of colourless crystals of melting point 152.5°–153° C.

(ii) In a manner analogous to that described in Example 3(ii), from rac-3'-acetyl-1',2',3',4'-tetrahydro-3'-hydroxy-5',8'-dimethoxyspiro[1,3-dithiolane-2,1'-naphthalene] there was obtained in 90% yield rac-3'-acetoxy-3'-acetyl-1',2',3',4'-tetrahydro-5',8'-dimethoxyspiro[1,3-dithiolane-2,1'-naphthalene] in the form of colourless crystals of melting point 162°–163° C.

EXAMPLE 6

(A) A solution of 0.757 g (3.4 mmol) of trans-1,2-diacetoxy-1,2-dihydrobenzocyclobutene and 0.970 g (3.1 mmol) of methyl rac-1',2',3',4',5',8'-hexahydro-5',8'-dioxospiro[1,3-dithiolane-2,4'-naphthalene]-2'-carboxylate [prepared as described in Example 2(A)] in 100 ml of dry xylene was stirred and heated under reflux under an atmosphere of nitrogen for 1 hour. The mixture was evaporated to dryness and the resulting brown oil was triturated with 10 ml of diethyl ether, cooled and filtered to give 1.02 g (61.5%) of methyl rac-1',2',3',4',5',5a',6',11',11a',12'-decahydro-6',11'-diacetoxy-5',12'-dioxospiro[1,3-dithiolane-2,4'-naphthacene]-2'-carboxylate in the form of a pale yellow solid of melting point 174°–175° C.

(B) (a) A solution of 32 mg (0.06 mmol) of methyl rac-1',2',3',4',5',5a',6',11',11a',12'-decahydro-6',11'-diacetoxy-5',12'-dioxospiro[1,3-dithiolane-2,4'-naphthacene]-2'-carboxylate in 2 ml of dry xylene was stirred and heated under reflux under an atmosphere of nitrogen for 20 hours. The solution was then evaporated to dryness to give 24 mg (97%) of methyl rac-1',2',3',4',5',12'-hexahydro-5',12'-dioxospiro[1,3-dithiolane-2,4'-naphthacene]-2'-carboxylate in the form of a bright yellow solid of melting point 216° C.

(b) A mixture of 26.5 mg (0.05 mmol) of methyl rac-1',2',3',4',5',5a',6',11',11a',12'-decahydro-6',11'-diacetoxy-5',12'-dioxospiro[1,3-dithiolane-2,4'-naphthacene]-2'-carboxylate and 5 mg (0.125 mmol) of sodium hydroxide in 2 ml of methanol was stirred at 20° C. for 1.5 hours. The mixture was then diluted with 10 ml of water and extracted with two 10 portions of dichloromethane. The combined dichloromethane extracts were washed with 10 ml of water, dried over magnesium sulphate and evaporated to dryness to give 15 mg (73%) of methyl rac-1',2',3',4',5',12'-hexahydro-5',12'-dioxospiro[1,3-dithiolane-2,4'-naphthacene]-2'-carboxylate in the form of a bright yellow solid of melting point 216° C.

EXAMPLE 7

(A) A solution of 220 mg (1.0 mmol) of trans-1,2-diacetoxy-1,2-dihydrobenzocyclobutene and 234 mg (0.66 mmol) of rac-3'-acetoxy-3'-acetyl-1',2',3',4',5',8'-hexahydro-5',8'-dioxospiro[1,3-dithiolane-2,1'-naphthalene] [prepared as described in Example 5(A)] in 15 ml of dry xylene was stirred and heated under reflux under an atmosphere of nitrogen for 30 minutes. The pale orange solution was evaporated and the resulting yellow oil was triturated with 15 ml of diethyl ether to yield 298 mg (79%) of rac-3',6',11'-triacetoxy-3'-acetyl-1',2',3',4',5',5a',6',11',11a',12'-decahydro-5',12'-dioxospiro[1,3-dithiolane-2,1'-naphthacene] in the form of a pale yellow solid of melting point 135°–145° C.

(B) In a manner analogous to that described in Example 6(B) (a) or (b), from rac-3',6',11'-triacetoxy-3'-acetyl-1',2',3',4',5',5a',6',11',11a',12'-decahydro-5',12'-dioxospiro[1,3-dithiolane-2,1'-naphthacene] there can be obtained rac-3'-acetoxy-3'-acetyl-1',2',3',4',5',12'-hexahydro-5',12'-dioxospiro[1,3-dithiolane-2,1'-naphthacene].

EXAMPLE 8

(A) In a manner analogous to that described in Example 1(A), from rac-3-acetoxy-3-acetyl-1,1-ethylenedioxy-1,2,3,4-tetrahydro-5,8-dimethoxynaphthalene there was obtained in 93% yield rac-3-acetoxy-3-acetyl-1,1-ethylenedioxy-1,2,3,4,5,8-hexahydro-5,8-dioxonaphthalene in the form of a yellow solid of melting point 169°–171° C.

(B) A solution of 110 mg (0.5 mmol) of trans-1,2-diacetoxy-1,2-dihydrobenzocyclobutene and 112 mg (0.35 mmol) of rac-3-acetoxy-3-acetyl-1,1-ethylenedioxy-1,2,3,4,5,8-hexahydro-5,8-dioxonaphthalene in 10 ml of toluene was stirred and heated under reflux for 3 hours under an atmosphere of nitrogen. The solution was evaporated and the resulting yellow gum was crystallised from diethyl ether to yield 80 mg (42%) of rac-3,6,11-triacetoxy-3-acetyl-1,1-ethylenedioxy-1,2,3,4,5,5a,6,11,11a,12-decahydro-5,12-dioxonaphthacene in the form of a pale yellow solid of melting point 133°–143° C.

(C) In a manner analogous to that described in Example 6(B) (a) or (b), from rac-3,6,11-triacetoxy-3-acetyl-1,1-ethylenedioxy-1,2,3,4,5,5a,6,11,11a,12-decahydro-5,12-dioxonaphthacene there can be obtained rac-3- acetoxy-3-acetyl-1,1-ethylenedioxy-1,2,3,4,5,12-hexahydro-5,12-dioxonaphthacene.

The rac-3-acetoxy-3-acetyl-1,1-ethylenedioxy-1,2,3,4-tetrahydro-5,8-dimethoxynaphthalene used as the starting material in part (A) of this Example can be prepared as follows:

(i) In a manner analogous to that described in Example 5(i), from methyl rac-4,4-ethylenedioxy-1,2,3,4-tetrahydro-2-hydroxy-5,8-dimethoxynaphthalene-2-carboxylate [prepared as described in Example 4(ii) (a) or (b)] there was obtained in 66% yield rac-3-acetyl-1,1-ethylenedioxy-1,2,3,4-tetrahydro-3-hydroxy-5,8-dimethoxynaphthalene in the form of colourless crystals of melting point 59°–60° C.

(ii) In a manner analogous to that described in Example 3(ii), from rac-3-acetyl-1,1-ethylenedioxy-1,2,3,4-tetrahydro-3-hydroxy-5,8-dimethoxynaphthalene there was obtained in 75% yield rac-3-acetoxy-3-acetyl-1,1-ethylenedioxy-1,2,3,4-tetrahydro-5,8-dimethoxynaphthalene in the form of colourless crystals of melting point 144°–146° C.

EXAMPLE 9

(A) In a manner analogous to that described in Example 1(A), from methyl rac-4,4-ethylenedioxy-1,2,3,4-tetrahydro-2-hydroxy-5,8-dimethoxynaphthalene-2-carboxylate [prepared as described in Example 4(ii) (a) or (b)] there was obtained in 43% yield, after purification by chromatography on silica gel, methyl rac-4,4-ethylenedioxy-1,2,3,4,5,8-hexahydro-2-hydroxy-5,8-dioxonaphthalene-2-carboxylate in the form of bright yellow crystals of melting point 111°–113° C.

(B) A solution of 200 mg of trans-1,2-diacetoxy-1,2-dihydrobenzocyclobutene and 100 mg of methyl rac-4,4-ethylenedioxy-1,2,3,4,5,8-hexahydro-2-hydroxy-5,8-dioxonaphthalene-2-carboxylate in 10 ml of xylene was stirred and heated under reflux for 1.5 hours under an atmosphere of nitrogen. The solution was evaporated to give a bright yellow crystalline residue. Trituration of this residue with diethyl ether gave 100 mg (74.5%) of methyl rac-4,4-ethylenedioxy-1,2,3,4,5,12-hexahydro-2-hydroxy-5,12-dioxonaphthacene-2-carboxylate in the form of yellow crystals of melting point 207°–209° C.

EXAMPLE 10

A mixture of 240 mg (1.1 mmol) of trans-1,2-diacetoxy-1,2-dihydrobenzocyclobutene and 220 mg (1.0 mmol) of methyl rac-1,2,3,4,5,8-hexahydro-5,8-dioxonaphthalene-2-carboxylate in 20 ml of dry xylene was stirred and heated under reflux under an atmosphere of nitrogen for 18 hours. The solution was evaporated to dryness, the yellow residue was stirred with 10 ml of diethyl ether and the mixture was subsequently filtered to give 260 mg (81%) of methyl rac-1,2,3,4,5,12-hexahydro-5,12-dioxonaphthacene-2-carboxylate in the form of a bright yellow solid of melting point 173°–174° C.

EXAMPLE 11

A mixture of 70 mg (0.32 mmol) of trans-1,2-diacetoxy-1,2-dihydrobenzocyclobutene and 66 mg (0.21 mmol) of methyl rac-1',2',3',4',5',8'-hexahydro-5',8'-dioxospiro[1,3-dithiolane-2,4'-naphthalene]-2'-carboxylate [prepared as described in Example 2(A)] in 5 ml of xylene was stirred and heated under reflux under an atmosphere of nitrogen for 23 hours. The mixture was evaporated to dryness and the residue was stirred with 5 ml of diethyl ether and then filtered to give 52 mg (60%) of methyl rac-1',2',3',4',5',12'-hexahydro-5',12'-dioxospiro[1,3-dithiolane-2,4'-naphthacene]-2'-carboxylate in the form of a bright yellow solid of melting point 216° C.

EXAMPLE 12

A mixture of 0.825 g (0.00375 mol) of trans-1,2-diacetoxy-1,2-dihydrobenzocyclobutene and 1.20 g (0.0034 mol) of rac-3'-acetoxy-3'-acetyl-1',2',3',4',5',8'-hexahydro-5',8'-dioxospiro[1,3-dithiolane-2,1'-naphthalene] [prepared as described in Example 5(A)] in 65 ml of xylene was stirred and heated under reflux under an atmosphere of nitrogen for 16 hours. The solution was evaporated to dryness and the residue was stirred with 20 ml of diethyl ether and filtered to give 1.259 g (82%) of rac-3'-acetoxy-3'-acetyl-1',2',3',4',5',12'-hexahydro-5',12'-dioxospiro[1,3-dithiolane-2,1'-naphthacene] in the form of a bright yellow solid of melting point 239°–241° C.

EXAMPLE 13

A mixture of 165 mg (0.75 mmol) of trans-1,2-diacetoxy-1,2-dihydrobenzocyclobutene and 160 mg (0.50 mmol) of rac-3-acetoxy-3-acetyl-1,1-ethylenedioxy-1,2,3,4,5,8-hexahydro-5,8-dioxonaphthalene [prepared as described in Example 7(A)] in 15 ml of xylene was stirred and heated under reflux under an atmosphere of nitrogen for 16 hours. The solution was evaporated to dryness and the yellow residue was stirred with 5 ml of diethyl ether and filtered to give 119 mg (57%) of rac-3-acetoxy-3-acetyl-1,1-ethylenedioxy-1,2,3,4,5,12-hexahydro-5,12-dioxonaphthacene in the form of a bright yellow solid of melting point 232°–236° C.

EXAMPLE 14

(A) A solution of 7.33 g of ammonium ceric nitrate in 100 ml of water was added over a period of 5 minutes to a stirred solution of 2.06 g of rac-cis-3-(1,1-ethylenedioxyethyl)-1,2,3,4-tetrahydro-5,8-dimethoxynaphthalene-1,3-diol in 100 ml of acetonitrile. After a further 5 minutes, the mixture was poured into 500 ml of water and the product was extracted with six 150 ml portions of dichloromethane. The combined dichloromethane extracts were dried over magnesium sulphate and evaporated to give 2.0 g of rac-cis-3-(1,1-ethylenedioxyethyl)-1,2,3,4,5,8-hexahydro-5,8-dioxonaphthalene-1,3-diol in the form of an orange gum which was dissolved in 150 ml of xylene and used directly in the next step.

(B) 2.5 g of trans-1,2-diacetoxy-1,2-dihydrobenzocyclobutene were added to the solution of rac-cis-3-(1,1-ethylenedioxyethyl)-1,2,3,4,5,8-hexahydro-5,8-dioxonaphthalene-1,3-diol in xylene, prepared as described in the preceding paragraph, and the mixture was heated at 140° C. under an atmosphere of nitrogen for 1.75 hours. The solution was cooled and the solvent was evaporated to give a yellow crystalline product which was washed with diethyl ether and filtered to give 2.12 g (84%) of rac-cis-3-(1,1-ethylenedioxyethyl)-1,2,3,4,5,12-hexahydro-5,12-dioxonaphthacene-1,3-diol in the form of yellow crystals of melting point 217°–218° C. Recrystallisation from tetrahydrofuran/isopropanol raised the melting point to 221°–223° C.

0.5 g of rac-cis-3-(1,1-ethylenedioxyethyl)-1,2,3,4,5,12-hexahydro-5,12-dioxonaphthacene-1,3-diol was dissolved in 140 ml of dioxan and 40 ml of concentrated hydrochloric acid and 400 ml of water were added. The mixture was stirred at room temperature for 5 hours and then poured into 400 ml of water. The product was extracted into three 150 ml portions of dichloromethane, the combined dichloromethane extracts were washed with 10% potassium hydrogen carbonate solution, dried and evaporated to give orange-yellow crystals. Recrystallisation from dichloromethane/diethyl ether gave 358 mg (81%) of rac-cis-3-acetyl-1,2,3,4,5,12-hexahydro-5,12-dioxonaphthacene-1,3-diol in the form of yellow crystals of melting point 253°–253.5° C.

The rac-cis-3-(1,1-ethylenedioxyethyl)-1,2,3,4-tetrahydro-5,8-dimethoxynaphthalene-1,3-diol used as the starting material in part (A) of this Example can be prepared as follows:

(i) 2.0 g of rac-3'-acetyl-1',2',3',4'-tetrahydro-3'-hydroxy-5',8'-dimethoxyspiro[1,3-dithiolane-2,1'-naphthalene] [prepared as described in Example 5(i)] were dissolved in 150 ml of benzene containing 15 ml of ethyleneglycol, 80 mg of toluene-4-sulphonic acid and 5 ml of acetone. The mixture was heated under reflux for 6 hours using a Dean-Stark water separator and then cooled to room temperature. The mixture was washed with two 100 ml portions of 10% aqueous potassium hydrogen carbonate and two 100 ml portions of water, dried over magnesium sulphate and evaporated to give a white foam. Trituration with diethyl ether gave rac-3'-(1,1-ethylenedioxyethyl)-1',2',3',4'-tetrahydro-3'-hydroxy-5',8'-dimethoxyspiro[1,3-dithiolane-2,1'-naphthalene] in the form of colourless crystals of melting point 162.5°–163° C.

(ii) 2.0 g of rac-3'-(1,1-ethylenedioxyethyl)-1',2',3',4'-tetrahydro-3'-hydroxy-5',8'-dimethoxyspiro[1,3-dithiolane-2,1'-naphthalene] in 20 ml of tetrahydrofuran were added over a period of 10 minutes to a suspension of 6.4 g of mercuric oxide and 6.4 g of mercuric chloride in 200 ml of methanol and 18 ml of water. The resulting suspension was stirred at room temperature for 1.25 hours and then ca 100 ml of solvent were removed by evaporation under reduced pressure. 300 ml of dichloromethane were added and the suspension obtained was filtered to remove insoluble mercury salts. The filtrate was washed with three 200 ml portions of water, dried over magnesium sulphate and evaporated to give a solid residue. Trituration with diethyl ether gave 1.42 g (89%) of rac-3-(1,1-ethylenedioxyethyl)-1,2,3,4-tetrahydro-3-hydroxy-5,8-dimethoxy-1-oxo-naphthalene in the form of an off-white powder of melting point 177.5°–178° C.

(iii) 6.1 g of rac-3-(1,1-ethylenedioxyethyl)-1,2,3,4-tetrahydro-3-hydroxy-5,8-dimethoxy-1-oxo-naphthalene were dissolved in 32 ml of dry tetrahydrofuran and 1.2 g of lithium borohydride were added. The mixture obtained was stirred at room temperature under an atmosphere of nitrogen for 3.5 hours and then a further 400 mg of lithium borohydride were added. After 30 minutes, the solvent was evaporated and the residue was taken up in 100 ml of ethyl acetate and 100 ml of 5% aqueous ammonium chloride. The aqueous layer was extracted with three 50 ml portions of ethyl acetate and the combined extracts were washed with brine, dried and evaporated. The oily residue was dissolved in 200 ml of dry ethyl acetate and 1.8 g of benzeneboronic acid and 10 drops of acetic acid were added. The mixture was heated under reflux in a nitrogen atmosphere for 1 hour, cooled, washed with 10% potassium hydrogen carbonate solution, dried and evaporated. The product was separated on a silica gel column (2.5 cm×20 cm) using hexane/ethyl acetate [(1:1, 75 ml fractions] for the first 12 fractions and then ethyl acetate. 4.3 g (55%) of rac-cis-3-(1,1-ethylenedioxyethyl)-1,2,3,4-tetrahydro-5,8-dimethoxynaphthalene-1,3-diyl benzeneboronate of melting point 149°–149.5° C. were obtained from fractions 2–8 and 1.8 g (29.5%) of rac-trans-3-(1,1-ethylenedioxyethyl)-1,2,3,4-tetrahydro-5,8-dimethoxynaphthalene-1,3-diol of melting point 125.5°–126° C. were obtained from fractions 10–16.

(iv) 62 mg of rac-trans-3-(1,1-ethylenedioxyethyl)-1,2,3,4-tetrahydro-5,8-dimethoxynaphthalene-1,3-diol and 30 mg of benzeneboronic acid were dissolved in 10 ml of benzene and 5 mg of toluene-4-sulphonic acid were added while stirring. The resulting mixture was left to stand at room temperature overnight and was then washed with 5 ml of 10% potassium hydrogen carbonate solution. After drying, the solvent was evaporated and the residue was triturated with diethyl ether/hexane to give 63 mg (79.5%) of rac-cis-3-(1,1-ethylenedioxyethyl)-1,2,3,4-tetrahydro-5,8-dimethoxynaphthalene-1,3-diyl benzeneboronate which was identical with the compound obtained according to the preceding paragraph.

(v) 4.3 g of rac-cis-3-(1,1-ethylenedioxyethyl)-1,2,3,4-tetrahydro-5,8-dimethoxynaphthalene-1,3-diyl benzeneboronate were dissolved in 22 ml of dichloromethane containing 1 ml of acetic acid. 22 ml of 2-methyl-2,4-pentanediol were added and the resulting solution was left to stand at room temperature for 30 hours. The mixture was poured into 100 ml of 5% potassium hydrogen carbonate solution and extracted with four 100 ml portions of dichloromethane. The combined extracts were dried over magnesium sulphate and evaporated to give a colourless oil which was dissolved in 100 ml of hexane. The solution was seeded and the product was allowed to crystallise at 4° C. overnight. The product was collected and dried in vacuo to give 2.65 g (79%) of rac-cis-3-(1,1-ethylenedioxyethyl)-1,2,3,4-tetrahydro-5,8-dimethoxynaphthalene-1,3-diol of melting point 127°–127.5° C.

EXAMPLE 15

(A) A solution of 220 mg of ammonium ceric nitrate in 4 ml of water was added to a stirred solution of 62 mg of rac-trans-3-(1,1-ethylenedioxyethyl)-1,2,3,4-tetrahydro-5,8-dimethoxynaphthalene-1,3-diol in 4 ml of acetonitrile. After stirring for 5 minutes, the mixture was poured into 50 ml of water and extracted with six 25 ml portions of dichloromethane. The combined organic extracts were dried over magnesium sulphate and evaporated to give 55 mg of rac-trans-3-(1,1-ethylendioxyethyl)-1,2,3,4,5,8-hexahydro-5,8-dioxonaphthalene-1,3-diol in the form of an orange gum which was dissolved in 5 ml of xylene and used directly in the next step.

(B) The solution obtained according to the preceding paragraph was treated with 100 mg of trans-1,2-diacetoxy-1,2-dihydrobenzocyclobutene and the mixture was heated under reflux for 1 hour. After cooling, the solution was washed with dilute aqueous triethylamine and water, dried and then evaporated to give a yellow solid which was triturated with diethyl ether and then filtered to give 31 mg (41%) of rac-trans-3-(1,1-ethylenedioxyethyl)-1,2,3,4,5,12-hexahydro-5,12-dioxonaphthacene-1,3-diol in the form of orange-yellow crystals of melting point 246°–248° C.

EXAMPLE 16

In a manner analogous to that described in Example 14(A) and (B), from (1R,3R)-cis-3-(1,1-ethylenedioxyethyl)-1,2,3,4-tetrahydro-5,8-dimethoxynaphthalene-1,3-diol and (1S,3S)-cis-3-(1,1-ethylenedioxyethyl)-1,2,3,4-tetrahydro-5,8-dimethoxynaphthalene-1,3-diol there can respectively be obtained (1R,3R)-cis-3-(1,1-ethylendioxyethyl)-1,2,3,4,5,12-hexahydro-5,12-dioxonaphthacene-1,3-diol of melting point 212°–214° C.; $[\alpha]_D^{20} = -26.5°$ (c=0.5% in dioxan); and (1S,3S)-cis-3-(1,1-ethylenedioxyethyl)-1,2,3,4,5,12-hexahydro-5,12-dioxonaphthacene-1,3-diol of melting point 215°–216° C.; $[\alpha]_D^{20} = +27.6°$ (c=0.5% in dioxan).

The foregoing ketals can be treated with dilute hydrochloric acid in dioxan in a manner analogous to that described in the second paragraph of Example 14(B) to give, respectively:

(1R,3R)-cis-3-acetyl-1,2,3,4,5,12-hexahydro-5,12-dioxonaphthacene-1,3-diol; and (1S,3S)-cis-3-acetyl-1,2,3,4,5,12-hexahydro-5,12-dioxonaphthacene-1,3diol; melting point 193°–195° C.; $[\alpha]_D^{20} = +67.6°$ (c=0.5% in dioxan).

The (1R,3R)-cis and (1S,3S)-cis diols used as the starting materials in this Example can be prepared as follows:

A suspension of 3.42 g of rac-1',2',3',4'-tetrahydro-2'-hydroxy-5',8'-dimethoxyspiro[1,3-dithiolane-2,4'-naphthalene]-2'-carboxylic acid [prepared as described in Example 4(iii)] and 4.0 g of brucine was heated under reflux until a clear solution was obtained. After seeding, the solution was left to cool slowly to room temperature. The crystalline precipitate (3.6 g) was collected after 2 days. The precipitate was dissolved in 1500 ml of boiling ethyl acetate, the solution was concentrated to 600 ml and left to cool slowly. The crystalline product [2.7 g $[\alpha]_D^{20} = -46.6°$, c=0.5% in dimethylformamide] was suspended in 150 ml of ethyl acetate and shaken with three 10 ml portions of 5-M hydrochloric acid and with two 100 ml portions of brine. After drying over magnesium sulphate, the solvent was evaporated to give a colourless oil which was crystallised from diethyl ether to yield 1.22 g of (R)-1',2',3',4'-tetrahydro-2'-hydroxy-5',8'-dimethoxyspiro[1,3-dithiolane-2,4'-naphthalene]-2'-carboxylic acid in the form of colourless crystals of melting point 147°–149° C.; $[\alpha]_D^{20} = +13.8°$, c=0.5% in dioxan.

The ethyl acetate mother liquors from the first crystallisation were shaken with three 10 ml portions of 5-M hydrochloric acid and with two 100 ml portions of brine, dried and evaporated to give 1.7 g of a solid residue. The residue was suspended in 50 ml of ethyl acetate and heated under reflux for 0.5 hour. After cooling, 0.6 g of rac-1',2',3',4'-tetrahydro-2'-hydroxy-5',8'-dimethoxyspiro[1,3-dithiolane-2,4'-naphthalene]-2'-carboxylic acid of melting point 189°–190° C. was obtained. The mother liquors were evaporated and the residue was taken up in diethyl ether, filtered, and the product crystallised to give 1.12 g of (S)-1',2',3',4'-tetrahydro-2'-hydroxy-5',8'-dimethoxyspiro[1,3-dithiolane-2,4'-naphthalene]-2'-carboxylic acid in the form of colourless crystals of melting point 145°–148° C.; $[\alpha]_D^{20} = -13.5°$, c=0.5% in dioxan.

The foregoing (R) and (S) acids were separately converted into the corresponding methyl esters according to the procedure described in Example 4(iv) and the methyl esters were separately converted into the corresponding methyl ketones according to the procedure described in Example 5(i). There were obtained:

(R)-3'-acetyl-1',2',3',4'-tetrahydro-3'-hydroxy-5',8'-dimethoxyspiro[1,3-dithiolane-2,1'-naphthalene] in 53% yield in the form of colourless crystals of melting point 178°–180° C.; $[\alpha]_D^{20} = +23.7°$, c=0.5% in chloroform; and (S)-3'-acetyl-1',2',3',4'-tetrahydro-3'-hydroxy-5',8'-dimethoxyspiro[1,3-dithiolane-2,1'-naphthalene] in 52% yield in the form of colourless crystals of melting point 178°–180° C.; $[\alpha]_D^{20} = -23.8°$, c=0.5% in chloroform.

By ketalising the foregoing methyl ketones in a manner analogous to that described in Example 14(i), there were obtained:

(R)-3'-(1,1-ethylenedioxyethyl)-1',2',3',4'-tetrahydro-3'-hydroxy-5',8'-dimethoxyspiro[1,3-dithiolane-2,1'-naphthalene] of melting point 143°–145° C.; $[\alpha]_D^{20} = +42.6°$ (c=0.5% in chloroform); and (S)-3'-(1,1-ethylenedioxyethyl)-1',2',3',4'-tetrahydro-3'-hydroxy-5',8'-dimethoxyspiro[1,3-dithiolane-2,1'-naphthalene] of melting point 144°–146° C.; $[\alpha]_D^{20} = -42.4°$ (c=0.5% in chloroform).

The compounds prepared according to the preceding paragraph are treated with a mixture of mercuric oxide and mercuric chloride in a manner analogous to that described in Example 14(ii) to give:

(R)-3-(1,1-ethylenedioxyethyl)-1,2,3,4-tetrahydro-3-hydroxy-5,8-dimethoxy-1-oxo-naphthalene of melting point 183°–184° C.; $[\alpha]_D^{20} = -12.9°$ (c=0.5% in chloroform); and (S)-3-(1,1-ethylenedioxyethyl)-1,2,3,4-tetrahydro-3-hydroxy-5,8-dimethoxy-1-oxo-naphthalene of melting point 182.5°–184° C.; $[\alpha]_D^{20} = +14.0°$ (c=0.5% in chloroform).

According to the procedure described in Example 14(iii), from the compounds prepared according to the preceding paragraph there were obtained:

(1R,3R)-cis-3-(1,1-ethylenedioxyethyl)-1,2,3,4-tetrahydro-5,8-dimethoxynaphthalene-1,3-diyl benzeneboronate of melting point 124°–125° C.; $[\alpha]_D^{20} = -37.7°$ (c=0.5% in chloroform); and (1S,3S)-cis-3-(1,1-ethylenedioxyethyl)-1,2,3,4-tetrahydro-5,8-dimethoxynaphthalene-1,3-diyl benzeneboronate of melting point 124°–126° C.; $[\alpha]_D^{20} = +36.7°$ (c=0.5% in chloroform).

According to the procedure described in Example 14(v), from the foregoing benzeneboronates there were obtained:

(1R,3R)-cis-3-(1,1-ethylenedioxyethyl)-1,2,3,4-tetrahydro-5,8-dimethoxynaphthalene-1,3-diol of melting point 143.5°–144.5° C.; $[\alpha]_D^{20} = -5.7°$ (c=0.5% in chloroform); and (1S,3S)-cis-3-(1,1-ethoxyenedioxyethyl)-1,2,3,4-tetrahydro-5,8-dimethoxynaphthalene-1,3-diol of melting point 143°–144° C.; $[\alpha]_D^{20} = +6.3°$ (c=0.5% in chloroform).

EXAMPLE 17

(A) 660 mg of (1R,3R)-cis-3-acetyl-1,2,3,4,5,12-hexahydro-5,12-dioxonaphthacene-1,3-diol, prepared as described in Example 16, in 140 ml of chloroform were treated with 40 drops of bromine and the mixture was left to stand at room temperature in the dark for 24 hours. Removal of the solvent and trituration of the residue with diethyl ether gave 750 mg (92%) of (1R,3R)-cis-3-bromoacetyl-1,2,3,4,5,12-hexahydro-5,12-dioxonaphthacene-1,3-diol in the form of a yellow powder of melting point 207°–208° C. (decomposition).

In an analogous manner, from (1S,3S)-cis-3-acetyl-1,2,3,4,5,12-hexahydro-5,12-dioxonaphthacene-1,3-diol there was obtained (1S,3S)-cis-3-bromoacetyl- 1,2,3,4,5,12-hexahydro-5,12-dioxonaphthacene-1,3-diol of melting point 205°–207° C. (decomposition), and from rac-cis-3-acetyl-1,2,3,4,5,12-hexahydro-5,12-dioxonaphthacene-1,3-diol there was obtained rac-cis-3-bromoacetyl-1,2,3,4,5,12-hexahydro-5,12-dioxonaphthacene-1,3-diol which, after recrystallisation from tetrahydrofuran/hexane, gave yellow crystals of melting point 208°–208.5° C. (decomposition).

(B) (i) 100 mg of (1R,3R)-cis-3-bromoacetyl-1,2,3,4,5,12-hexahydro-5,12-dioxonaphthacene-1,3-diol were suspended in 30 ml of acetic acid containing 300 mg of silver acetate. The mixture was heated at 90° C. in the dark for 4.5 hours. The solvent was removed and the residue was purified on a silica gel column. There were obtained 76 mg (88%) of (1R,3R)-cis-3-(2-acetoxyacetyl)-1,2,3,4,5,12-hexahydro-5,12-dioxonaphthacene-1,3-diol in the form of a yellow solid of melting point 186°–190° C.

In an analogous manner, from (1S,3S)-cis-3-bromoacetyl-1,2,3,4,5,12-hexahydro-5,12-dioxonaphthacene-1,3-diol there was obtained (1S,3S)-cis-3-(2-acetoxyacetyl)-1,2,3,4,5,12-hexahydro-5,12-dioxonaphthacene-1,3-diol of melting point 188°–190° C., and from rac-cis-3-bromoacetyl-1,2,3,4,5,12-hexahydro-5,12-dioxonaphthacene-1,3-diol there was obtained rac-cis-3-(2-acetoxyacetyl)-1,2,3,4,5,12-hexahydro-5,12-dioxonaphthacene-1,3-diol of melting point 217°–220° C.

(B) (ii) 750 mg of (1R,3R)-cis-3-bromoacetyl-1,2,3,4,5,12-hexahydro-5,12-dioxonaphthacene-1,3-diol were suspended in 200 ml of acetonitrile containing 20 drops of valeric acid and 0.5 g of silver valerate. The mixture was stirred at room temperature for 3.5 hours in the dark, filtered and the solvent was removed by evaporation. The dark residue was purified by column chromatography on silica gel using ethyl acetate/hexane (1:1) for the elution. 580 mg (74%) of (1R,3R)-cis-1,2,3,4,5,12-hexahydro-3-(2-valeryloxyacetyl)-5,12-dioxonaphthacene-1,3-diol were obtained in the form of yellow crystals from diethyl ether; melting point 174°–175° C.

In an analogous manner, from (1S,3S)-cis-3-bromoacetyl-1,2,3,4,5,12-hexahydro-5,12-dioxonaphthacene-1,3-diol there was obtained (1S,3S)-cis-1,2,3,4,5,12-hexahydro-3-(2-valeryloxyacetyl)-5,12-dioxonaphthacene-1,3-diol of melting poiint 175°–176° C.

EXAMPLE 18

50 mg of rac-cis-3-bromoacetyl-1,2,3,4,5,12-hexahydro-5,12-dioxonaphthacene-1,3-diol were dissolved in 5 ml of dimethyl sulphoxide and 40 mg of silver trifluoroacetate were added to the solution. The resulting mixture was stirred for 4 hours in the dark under nitrogen and then poured into 50 ml of water. The solution was extracted with 50 ml of dichloromethane and the extract was washed with three 25 ml portions of water, dried over magnesium sulphate and evaporated to give 25 mg (59%) of rac-cis-3-hydroxyacetyl-1,2,3,4,5,12-hexahydro-5,12-dioxonaphthacene-1,3-diol in the form of a yellow powder of melting point 175°–180° C. (decomposition) after trituration with diethyl ether.

EXAMPLE 19

(A) A solution of 1.1 g of ammonium ceric nitrate in 20 ml of water was added to a stirred solution of 296 mg of race-cis-3-acetoxymethyl-1,2,3,4-tetrahydro-5,8-dimethoxynaphthalene-1,3-diol in 20 ml of acetonitrile. After stirring at room temperature for 5 minutes, the mixture was poured into 200 ml of water and extracted with six 50 ml portions of dichloromethane. The combined organic extracts were dried over magnesium sulphate and evaporated to give rac-cis-3-acetoxymethyl-1,2,3,4,5,8-hexahydro-5,8-dioxonaphthalene-1,3-diol in the form of an orange gum which was dissolved in 20 ml of xylene. This solution was used directly in the next step.

(B) The solution obtained according to the preceding paragraph was treated with 0.3 g of trans-1,2-diacetoxy-1,2-dihydrobenzocyclobutene and the mixture was heated at 140° C. for 2 hours. After cooling, the solution was filtered through silica gel and the solvent was removed by evaporation to give a solid yellow residue. Trituration with ethyl acetate/diethyl ether gave 220 mg (60%) of rac-cis-3-acetoxymethyl-1,2,3,4,5,12-hexahydro-5,12-dioxonaphthacene-1,3-diol in the form of yellow crystals of melting point 222°–224° C.

The rac-cis-3-acetoxymethyl-1,2,3,4-tetrahydro-5,8-dimethoxynaphthalene-1,3-diol used as the starting material in part (A) of this Example can be prepared as follows:

(i) 2.0 g of methyl rac-1',2',3',4'-tetrahydro-2'-hydroxy-5',8'-dimethoxyspiro[1,3-dithiolane-2,4'-naphthalene]-2'-carboxylate, prepared as described in Example 4(iv), were dissolved in 200 ml of dry tetrahydrofuran and 2.0 g of sodium borohydride were added to the solution. The resulting mixture was stirred at room temperature under nitrogen for 20 hours. The solvent was removed by evaporation and 100 ml of 10% ammonium chloride solution were added. The mixture was extracted with three 30 ml portions of ethyl acetate. The extracts were dried and evaporated to give a colourless oil. Crystallisation of this oil from ethyl acetate/petroleum ether gave 1.6 g (87%) of rac-1',2',3',4'-tetrahydro-3'-hydroxy-3'-hydroxymethyl-5',8'-dimethoxyspiro[1,3-dithiolane-2,1'-naphthalene] of melting point 132.5°–133.5° C.

(ii) 1.6 g of rac-1',2',3',4'-tetrahydro-3'-hydroxy-3'-hydroxymethyl-5',8'-dimethoxyspiro[1,3-dithiolane-2,1'-naphthalene] were dissolved in 30 ml of dry pyridine and 1.5 g. of acetic anhydride were added to the solution. The mixture was left to stand at room temperature for 20 hours and then poured into ice-cold 5-M sulphuric acid. The resulting mixture was extracted with ethyl acetate, the extracts were washed with water and sodium hydrogen carbonate solution, dried and evaporated to give 1.8 g of rac-3'-acetoxymethyl-1',2',3',4'-tetrahydro-3'-hydroxy-5',8'-dimethoxyspiro[1,3-dithiolane-2,1'-naphthalene] in the form of a colourless oil which was used directly in the next step.

(iii) 1.9 g of rac-3'-acetoxymethyl-1',2',3',4'-tetrahydro-3'-hydroxy-5',8'-dimethoxyspiro[1,3-dithiolane-2,1'-napthalene] in 40 ml of tetrahydrofuran were added to a stirred suspension of 6.4 g of mercuric chloride and 6.4 g of mercuric oxide in 200 ml of methanol containing 18 ml of water. After standing at room temperature for 1 hour, ca 150 ml of solvent were removed by evaporation under reduced pressure, 200 ml of dichloromethane were added and the resulting suspension was filtered to remove insoluble material. The filtrate was washed with three 200 ml portions of water, dried over magnesium sulphate and evaporated to give a solid residue. Trituration with diethyl ether gave 1.0 g (70%) of rac-3-acetoxymethyl-1,2,3,4-tetrahydro-3-hydroxy-5,8-dimethoxy-1-oxo-naphthalene in the form of an off-white powder of melting point 124°–126° C.

(iv) 1.0 g of rac-3-acetoxymethyl-1,2,3,4-tetrahydro-3-hydroxy-5,8-dimethoxy-1-oxo-naphthalene was dissolved in 100 ml of dry tetrahydrofuran and 750 mg of sodium borohydride were added. The mixture was stirred at room temperature for 2 hours and the solvent was removed by evaporation. 100 ml of 10% ammonium chloride were added and the mixture was extracted with three 50 ml portions of ethyl acetate. The combined ethyl acetate extracts were washed with saturated sodium chloride solution, dried over magnesium sulphate and evaporated to give a clear colourless oil which was dissolved in 100 ml of ethyl acetate. 500 mg of benzeneboronic acid and 1 drop of acetic acid were added and the resulting solution was heated under reflux for 1 hour. After evaporation of the solvent, 500 mg of rac-cis-3-acetoxymethyl-1,2,3,4-tetrahydro-5,8-dimethoxynaphthalene-1,3-diyl benzeneboronate crystallised from diethyl ether in the form of colourless crystals. The mother liquors were evaporated and the residue was dissolved in 50 ml of benzene. After the addition of 25 mg of toluene-4-sulphonic acid, the solution was stirred at room temperature overnight. The solution was then washed with 10 ml of 10% potassium hydrogen carbonate solution, dried and evaporated. Crystallisation from diethyl ether gave a further 560 mg of the aforementioned benzeneboronate. The total yield was 1.06 g (81.5%); melting point 153°–154° C.

(v) 1.0 g of rac-cis-3-acetoxymethyl-1,2,3,4-tetrahydro-5,8-dimethoxynaphthalene-1,3-diyl benzeneboronate was dissolved in 6 ml of dichloromethane containing 0.5 ml of acetic acid. 6 ml of 2-methyl-2,4-pentanediol were added and the resulting solution was left to stand at room temperature for 24 hours. The mixture was poured into 50 ml of 5% potassium hydrogen carbonate solution and extracted with three 25 ml portions of dichloromethane. The combined extracts were dried over magnesium sulphate and evaporated to give a colourless oil which was dissolved in 50 ml of hexane. The product was allowed to crystallise at 4° C. overnight. Filtration gave 600 mg (77.5%) of rac-cis-3-acetoxymethyl-1,2,3,4-tetrahydro-5,8-dimethoxynaphthalene-1,3-diol in the form of colourless crystals of melting point 106°–107° C.

EXAMPLE 20

In a manner analogous to that described in Example 19(A) and (B), from rac-cis-1,2,3,4-tetrahydro-3-methyl-5,8-dimethoxynaphthalene-1,3-diol there was obtained rac-cis-1,2,3,4,5,12-hexahydro-3-methyl-5,12-dioxonaphthacene-1,3-diol in the form of yellow crystals of melting point 223°–224° C.

The rac-cis-1,2,3,4-tetrahydro-3-methyl-5,8-dimethoxynaphthalene-1,3-diol used as the starting material can be prepared as follows:

(i) 326 mg of rac-1',2',3',4'-tetrahydro-3'-hydroxy-3'-hydroxymethyl-5',8'-dimethoxyspiro[1,3-dithiolane-2,1'-naphthalene], prepared as described in part (i) of Example 19, were dissolved in 10 ml of pyridine and the solution was cooled to 0° C. 400 mg of toluene-4-sulphonyl chloride were added and the solution was held at 4° C. for 20 hours. The solution was poured on to crushed ice, acidified with 5-M sulphuric acid and extracted with ethyl acetate. The ethyl acetate extract was washed with water and then with 5% potassium hydrogen carbonate solution. After drying, the solvent was removed by evaporation to give a white solid. Trituration of this solid with diethyl ether gave 400 mg (83%) of rac-1',2',3',4'-tetrahydro-3'-hydroxy-5',8'-dimethoxyspiro[1,3-dithiolane-2,1'-naphthyl]-3'-methyl p-toluenesulphonate in the form of a crystalline powder of melting point 124°–126° C. (decomposition).

(ii) 200 mg of rac-1',2',3',4'-tetrahydro-3'-hydroxy-5',8'-dimethoxyspiro[1,3-dithiolane-2,1'-naphthyl]-3'-methyl p-toluenesulphonate were dissolved in 20 ml of dry tetrahydrofuran containing 100 mg of lithium aluminium hydride. The mixture was heated under reflux for 3.5 hours under a nitrogen atmosphere. The solution was cooled and quenched by the addition of saturated ammonium chloride solution. The solvent was removed by evaporation and the residue was taken up in dilute hydrochloric acid. The solution was extracted with ethyl acetate and the extracts were washed with water, dried and evaporated to give a colourless oil which crystallised from diethyl ether. There were obtained 100 mg (77.5%) of rac-1',2',3',4'-tetrahydro-3'-hydroxy-3'-methyl-5',8'-dimethoxyspiro[1,3-dithiolane-2,1'-naphthalene] in the form of colourless crystals of melting point 163°–165° C.

(iii) In a manner analogous to that described in Example 19(iii), from rac-1',2',3',4'-tetrahydro-3'-methyl-5',8'-dimethoxyspiro[1,3-dithiolane-2,1'-naphthalene] there was obtained rac-1,2,3,4-tetrahydro-3-methyl-5,8-dimethoxy-1-oxo-naphthalene which was used without purification.

(iv) In a manner analogous to that described in Example 19(iv), from rac-1,2,3,4-tetrahydro-3-methyl-5,8-dimethoxy-1-oxo-naphthalene there was obtained rac-cis-1,2,3,4-tetrahydro-3-methyl-5,8-dimethoxynaphthalene-1,3-diyl benzeneboronate in the form of colourless crystals of melting point 138°–139° C.

(v) In a manner analogous to that described in Example 19(v), from rac-cis-1,2,3,4-tetrahydro-3-methyl-5,8-dimethoxynaphthalene-1,3-diyl benzeneboronate there was obtained rac-cis-1,2,3,4-tetrahydro-3-methyl-5,8-dimethoxynaphthalene-1,3-diol in the form of colourless crystals of melting point 142°–144° C.

What is claimed:

1. A process for the manufacture of compounds of the general formula

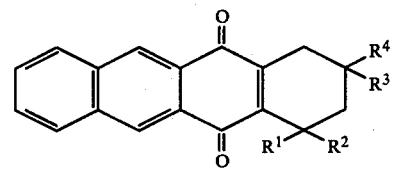

wherein one of $R^1$ and $R^2$ represents a hydrogen atom and the other represents a hydrogen atom or a hydroxy group or $R^1$ and $R^2$ together represent an ethylene ketal or ethylene thio ketal group, $R^3$ represents a hydrogen atom or a hydroxy or lower alkanoyloxy group and $R^4$ represents a lower alkyl or lowr alkoxycarbonyl or benzyloxycarbonyl group or a group of the formula

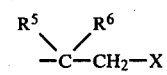

wherein $R^5$ and $R^6$ together form an oxo group or an ethylene ketal or ethylene thio ketal group and X represents a hydrogen atom or a hydroxy or lower alkanoyloxy group,
which comprises (a) eliminating 2 mols of the lower alkane carboxylic acid R⁷H from a compound of the general formula

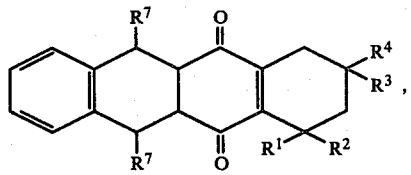

wherein $R^1$, $R^2$, $R^3$ and $R^4$ have the significance given earlier in this claim and $R^7$ represents a lower alkanoyloxy group,
by heating or treatment with an alkali metal hydroxide.

2. The process according to claim 1, wherein the compound of formula II is prepared by reacting a compound of the general formula

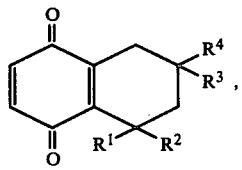

wherein $R^1$, $R^2$, $R^3$ and $R^4$ have the significance given in claim 1, with a trans compound of the general formula

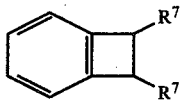

wherein $R^7$ has the significance given in claim 1.

3. The process according to claim 2, wherein the compound of formula V is prepared by reacting a compound of the general formula

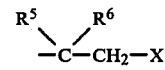

wherein one of $R^1$ and $R^2$ represents a hydrogen atom and the other represents a hydrogen atom or a hydroxy group or $R^1$ and $R^2$ together represent an ethylene ketal or ethylene thio ketal group, $R^3$ represents a hydrogen atom or a hydroxy or lower alkanoyloxy group and $R^4$ represents a lower alkyl or lower alkoxycarbonyl or benzyloxycarbonyl group or a group of the formula $$\begin{array}{c} R^5 \quad R^6 \\ \diagdown \diagup \\ -C-CH_2-X \end{array} \quad a$$

wherein $R^5$ and $R^6$ together form an oxo group or an ethylene ketal or ethylene thio ketal group and X represents a hydrogen atom or a hydroxy or lower alkanoyloxy group,
with ammonium ceric nitrate.

* * * * *